US012268765B2

(12) United States Patent
Hutton, III

(10) Patent No.: US 12,268,765 B2
(45) Date of Patent: Apr. 8, 2025

(54) PERSONAL CARE COMPOSITIONS SUBSTANTIALLY FREE OF SULFATED SURFACTANTS AND CONTAINING A GEL NETWORK

(71) Applicant: The Procter & Gamble Company, Cincinnati, OH (US)

(72) Inventor: Howard David Hutton, III, Oregonia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 42 days.

(21) Appl. No.: 17/327,972

(22) Filed: May 24, 2021

(65) Prior Publication Data

US 2021/0275410 A1    Sep. 9, 2021

Related U.S. Application Data

(63) Continuation of application No. 15/728,663, filed on Oct. 10, 2017, now abandoned.

(60) Provisional application No. 62/406,158, filed on Oct. 10, 2016, provisional application No. 62/414,940, filed on Oct. 31, 2016.

(51) Int. Cl.
*A61K 8/04* (2006.01)
*A61K 8/34* (2006.01)
*A61K 8/44* (2006.01)
*A61K 8/46* (2006.01)
*A61K 8/60* (2006.01)
*A61Q 5/02* (2006.01)

(52) U.S. Cl.
CPC .............. *A61K 8/042* (2013.01); *A61K 8/342* (2013.01); *A61K 8/44* (2013.01); *A61K 8/466* (2013.01); *A61K 8/602* (2013.01); *A61Q 5/02* (2013.01); *A61K 2800/33* (2013.01)

(58) Field of Classification Search
None
See application file for complete search history.

(56) References Cited

U.S. PATENT DOCUMENTS

| | | |
|---|---|---|
| 1,094,935 A | 4/1914 | Schenck et al. |
| 2,280,271 A | 4/1942 | Sullivan |
| 2,280,272 A | 4/1942 | Sullivan |
| 2,326,733 A | 8/1943 | Fisher |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | McCabe, Jr. |
| 2,658,072 A | 11/1953 | Kosmin |
| 2,694,668 A | 11/1954 | Fricke |
| 2,757,049 A | 7/1956 | Temple |
| 2,786,847 A | 3/1957 | Cislak |
| 2,798,053 A | 7/1957 | Brown |
| 2,809,971 A | 10/1957 | Jack |
| 2,826,551 A | 3/1958 | Geen |
| 3,152,046 A | 10/1964 | Maria |
| 3,155,591 A | 11/1964 | Harry |
| 3,194,540 A | 7/1965 | Hager |
| 3,236,733 A | 2/1966 | Karsten |
| 3,332,880 A | 7/1967 | Adriaan |
| 3,589,999 A | 6/1971 | Mcrae |
| 3,590,035 A | 6/1971 | Damico |
| 3,626,265 A | 12/1971 | Kraakman |
| 3,655,096 A | 4/1972 | Easter |
| 3,753,196 A | 8/1973 | Kurtz |
| 3,761,418 A | 9/1973 | Parran |
| 3,773,770 A | 11/1973 | Damico |
| 3,821,963 A | 7/1974 | Olson et al. |
| 3,852,441 A | 12/1974 | Kooistra |
| 3,929,678 A | 12/1975 | Laughlin et al. |
| 3,940,482 A | 2/1976 | Grand |
| 3,958,581 A | 5/1976 | Abegg |
| 3,959,461 A | 5/1976 | Bailey |
| 3,964,500 A | 6/1976 | Drakoff |
| 4,055,655 A | 10/1977 | Maurer |
| 4,089,945 A | 5/1978 | Brinkman |
| 4,152,416 A | 5/1979 | Marra |
| 4,161,426 A | 7/1979 | Kneer |
| 4,197,865 A | 4/1980 | Jacquet |
| 4,217,914 A | 8/1980 | Jacquet |
| 4,323,683 A | 4/1982 | Bolich, Jr. |
| 4,345,080 A | 8/1982 | Bolich, Jr. |
| 4,364,387 A | 12/1982 | Larkin |
| 4,379,753 A | 4/1983 | Bolich, Jr. |
| 4,381,919 A | 5/1983 | Jacquet |
| 4,387,090 A | 6/1983 | Bolich, Jr. |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,604,272 A | 8/1986 | Kratel |
| 4,608,183 A | 8/1986 | Rossmoore |
| 4,663,158 A | 5/1987 | Wolfram |
| 4,666,616 A | 5/1987 | Rossmoore |
| 4,670,430 A | 6/1987 | Imamura |

(Continued)

FOREIGN PATENT DOCUMENTS

| | | |
|---|---|---|
| AU | 2012337567 B2 | 4/2017 |
| CA | 2143558 A1 | 8/1996 |

(Continued)

OTHER PUBLICATIONS

De Meirleir et al. "Journal of Crystal Growth" 2013; 383: 51-56. (Year: 2013).

(Continued)

*Primary Examiner* — David J Blanchard
*Assistant Examiner* — Sarah J Chickos
(74) *Attorney, Agent, or Firm* — John G. Powell

(57) ABSTRACT

A personal care composition substantially free of sulfated surfactants includes a dispersed gel network, a detersive surfactant, and water. The dispersed gel network includes one or more fatty alcohols, a gel network surfactant, and water. Methods of making a personal care composition are also disclosed.

9 Claims, 1 Drawing Sheet

(56) References Cited

U.S. PATENT DOCUMENTS

| | | |
|---|---|---|
| 4,686,254 A | 8/1987 | Lochhead |
| 4,704,272 A | 11/1987 | Oh |
| 4,708,863 A | 11/1987 | Bews |
| 4,726,915 A | 2/1988 | Verdicchio |
| 4,788,006 A | 11/1988 | Bolich, Jr. |
| 4,834,767 A | 5/1989 | Helioff |
| 4,885,107 A | 12/1989 | Wetzel |
| 4,898,585 A | 2/1990 | Borsanyi |
| 4,995,804 A | 2/1991 | Hirabayashi |
| 5,034,218 A | 7/1991 | Duvel |
| 5,057,153 A | 10/1991 | Ruggiero |
| 5,104,646 A | 4/1992 | Bolich, Jr. |
| 5,106,609 A | 4/1992 | Bolich, Jr. |
| 5,106,613 A | 4/1992 | Hartnett |
| 5,114,898 A | 5/1992 | Pinnavaia |
| 5,154,847 A | 10/1992 | Lapetina |
| 5,186,928 A | 2/1993 | Birtwistle |
| 5,202,048 A | 4/1993 | Bartolo |
| 5,227,156 A | 7/1993 | Wiese |
| 5,248,445 A | 9/1993 | Rizvi |
| 5,273,189 A | 12/1993 | Jouillat et al. |
| RE34,584 E | 4/1994 | Grote |
| 5,358,667 A | 10/1994 | Bergmann |
| 5,360,581 A | 11/1994 | Rizvi |
| 5,373,973 A | 12/1994 | Foster |
| 5,462,589 A | 10/1995 | Nicholas |
| 5,466,425 A | 11/1995 | Adams |
| 5,478,501 A | 12/1995 | Rau |
| 5,495,538 A | 2/1996 | Fan |
| 5,518,774 A | 5/1996 | Kappock |
| 5,540,954 A | 7/1996 | Nicholas |
| 5,562,995 A | 10/1996 | Kappock |
| 5,609,862 A | 3/1997 | Chen et al. |
| 5,614,538 A | 3/1997 | Nelson, Jr. |
| 5,674,478 A | 10/1997 | Dodd et al. |
| 5,696,169 A | 12/1997 | Otsu |
| 5,710,114 A | 1/1998 | Pyles |
| 5,720,550 A | 2/1998 | Akiyama et al. |
| 5,726,137 A | 3/1998 | Patel |
| 5,750,122 A | 5/1998 | Evans |
| 5,756,076 A | 5/1998 | Cervantes |
| 5,776,444 A | 7/1998 | Birtwistle et al. |
| 5,785,962 A | 7/1998 | Hinz |
| 5,798,121 A | 8/1998 | Cauwet |
| 5,811,487 A | 9/1998 | Schulz, Jr. et al. |
| 5,836,479 A | 11/1998 | Klima et al. |
| 5,837,661 A | 11/1998 | Evans |
| 5,853,707 A | 12/1998 | Wells |
| 5,854,319 A | 12/1998 | Olenick, Jr. |
| 5,874,476 A | 2/1999 | Hsu |
| 5,876,705 A | 3/1999 | Uchiyama |
| 5,880,076 A | 3/1999 | Vermeer |
| 5,883,154 A | 3/1999 | Kappock |
| 5,885,948 A | 3/1999 | Glenn, Jr. et al. |
| 5,939,059 A | 8/1999 | Franklin |
| 5,939,203 A | 8/1999 | Kappock |
| 5,955,066 A | 9/1999 | Sako |
| 5,965,515 A | 10/1999 | Rau |
| 5,971,604 A | 10/1999 | Linga et al. |
| 5,977,036 A | 11/1999 | Guskey |
| 5,997,036 A | 12/1999 | Hamada |
| 5,997,851 A | 12/1999 | Cox |
| 6,017,562 A | 1/2000 | Kaufman |
| 6,034,043 A | 3/2000 | Fujiwara |
| 6,183,766 B1 | 2/2001 | Sine et al. |
| 6,303,109 B1 | 10/2001 | Foerster |
| 6,309,628 B1 | 10/2001 | Ansmann |
| 6,333,040 B1 | 12/2001 | Boyxen |
| 6,354,729 B1 | 3/2002 | Brown |
| RE37,793 E | 7/2002 | Domenico |
| 6,432,420 B2 | 8/2002 | Ellis |
| 6,432,421 B1 | 8/2002 | Brown |
| 6,451,300 B1 | 9/2002 | Dunlop et al. |
| 6,521,238 B1 | 2/2003 | Muller |
| 6,521,239 B1 | 2/2003 | Breton |
| RE38,130 E | 6/2003 | Adams |
| 6,616,325 B1 | 9/2003 | Brown |
| 6,719,967 B1 | 4/2004 | Brown |
| 6,774,096 B1 | 8/2004 | Paye |
| 6,878,368 B2 | 4/2005 | Ohta et al. |
| 6,908,912 B2 | 6/2005 | Rioux |
| 6,991,799 B2 | 1/2006 | Pham et al. |
| 7,294,611 B2 | 11/2007 | Metrot |
| 7,303,744 B2 | 12/2007 | Wells |
| 7,527,077 B2 | 5/2009 | McCall et al. |
| 7,531,497 B2 | 5/2009 | Midha et al. |
| 7,560,125 B2 | 7/2009 | Ananthapadmanabhan et al. |
| 7,776,347 B2 | 8/2010 | Kerschner et al. |
| 7,855,391 B2 | 12/2010 | Park et al. |
| 8,252,271 B2 | 8/2012 | Singer et al. |
| 8,349,300 B2 | 1/2013 | Wells |
| 8,349,301 B2 | 1/2013 | Wells |
| 8,349,302 B2 | 1/2013 | Johnson |
| 8,361,448 B2 | 1/2013 | Johnson |
| 8,361,449 B2 | 1/2013 | Wells |
| 8,361,450 B2 | 1/2013 | Johnson |
| 8,367,048 B2 | 2/2013 | Wells |
| 8,470,305 B2 | 6/2013 | Johnson |
| 8,635,014 B2 | 1/2014 | Jung |
| 8,653,014 B2 | 2/2014 | Hilvert |
| 8,655,819 B1 | 2/2014 | Burkard et al. |
| 8,663,612 B2 | 3/2014 | Gamez-Garcia et al. |
| 8,901,062 B2 | 12/2014 | De Meirleir et al. |
| 8,932,569 B2 | 1/2015 | Garrison et al. |
| 8,940,285 B2 | 1/2015 | Leray et al. |
| 8,969,261 B2 | 3/2015 | Talingting Pabalan et al. |
| 9,005,585 B2 | 4/2015 | Deckner et al. |
| 9,138,429 B2 | 9/2015 | Wise et al. |
| 9,381,382 B2 | 7/2016 | Schwartz et al. |
| 9,393,188 B2 | 7/2016 | Deckner et al. |
| 9,539,444 B2 | 1/2017 | Kinoshita |
| 9,587,209 B2 | 3/2017 | De Meirleir et al. |
| 9,724,283 B2 | 8/2017 | Rizk |
| 9,877,909 B2 | 1/2018 | Cetti et al. |
| 10,143,632 B2 | 12/2018 | Dihora et al. |
| 10,226,782 B2 | 3/2019 | Yamaguchi et al. |
| 10,689,183 B2 | 6/2020 | Moretti |
| 10,912,719 B2 | 2/2021 | Gulbin |
| 10,945,935 B2 | 3/2021 | Brown et al. |
| 2001/0047039 A1 | 11/2001 | Mcmanus |
| 2002/0119113 A1 | 8/2002 | Ellis |
| 2002/0131946 A1 | 9/2002 | Pham et al. |
| 2002/0169283 A1 | 11/2002 | Lu |
| 2002/0183300 A1 | 12/2002 | Fliss |
| 2003/0012646 A1 | 1/2003 | Liao |
| 2003/0017126 A1 | 1/2003 | Mahadeshwar |
| 2003/0044471 A1 | 3/2003 | Sakuma |
| 2003/0095938 A1 | 5/2003 | Casero |
| 2003/0119806 A1 | 6/2003 | Lindell |
| 2003/0130145 A1 | 7/2003 | Patel |
| 2003/0138497 A1 | 7/2003 | Sakuma |
| 2003/0171231 A1 | 9/2003 | Shana |
| 2003/0185779 A1 | 10/2003 | Mitsumatsu |
| 2003/0215522 A1 | 11/2003 | Johnson |
| 2003/0223952 A1 | 12/2003 | Wells et al. |
| 2003/0224954 A1 | 12/2003 | Wells et al. |
| 2003/0224955 A1 | 12/2003 | Ribery |
| 2004/0058855 A1 | 3/2004 | Schwartz |
| 2004/0092897 A1 | 5/2004 | Macedo, Jr. |
| 2004/0157754 A1 | 8/2004 | Geary et al. |
| 2004/0167114 A1 | 8/2004 | Fliss |
| 2004/0191331 A1 | 9/2004 | Schwartz |
| 2004/0197294 A1 | 10/2004 | Seipel |
| 2004/0223941 A1 | 11/2004 | Schwartz |
| 2004/0223991 A1 | 11/2004 | Wei et al. |
| 2004/0234471 A1 | 11/2004 | Corbella |
| 2004/0266886 A1 | 12/2004 | Seipel |
| 2005/0031569 A1 | 2/2005 | Seipel |
| 2005/0100570 A1 | 5/2005 | Wei et al. |
| 2005/0112083 A1 | 5/2005 | Wells et al. |
| 2005/0143268 A1 | 6/2005 | Midha |
| 2005/0181067 A1 | 8/2005 | Yokoyama |
| 2005/0196368 A1 | 9/2005 | Laurent et al. |
| 2005/0202984 A1 | 9/2005 | Schwartz |

(56) References Cited

U.S. PATENT DOCUMENTS

| | | |
|---|---|---|
| 2005/0267258 A1 | 12/2005 | Rajaraman et al. |
| 2006/0024256 A1 | 2/2006 | Wells |
| 2006/0024381 A1 | 2/2006 | Schwartz |
| 2006/0025256 A1 | 2/2006 | Wake |
| 2006/0045861 A1 | 3/2006 | Bejger |
| 2006/0078524 A1 | 4/2006 | Midha et al. |
| 2006/0078527 A1 | 4/2006 | Midha et al. |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0205631 A1 | 9/2006 | Smerznak et al. |
| 2006/0250658 A1 | 11/2006 | Jurgensen |
| 2006/0251605 A1 | 11/2006 | Belmar |
| 2006/0269501 A1 | 11/2006 | Johnson |
| 2006/0269502 A1 | 11/2006 | Johnson |
| 2007/0062906 A1 | 3/2007 | Morano et al. |
| 2007/0095721 A1 | 5/2007 | Davis et al. |
| 2007/0110696 A1 | 5/2007 | Johnson |
| 2007/0110700 A1 | 5/2007 | Wells |
| 2007/0128147 A1 | 6/2007 | Schwartz et al. |
| 2007/0280976 A1 | 12/2007 | Taylor et al. |
| 2008/0039352 A1 | 2/2008 | Wells et al. |
| 2008/0096786 A1 | 4/2008 | Holt et al. |
| 2008/0152611 A1 | 6/2008 | Wells et al. |
| 2008/0187507 A1 | 8/2008 | Johnson |
| 2010/0061952 A1 | 3/2010 | Wells et al. |
| 2010/0226868 A1 | 9/2010 | Gamez-Garcia et al. |
| 2010/0234260 A1 | 9/2010 | Sekine et al. |
| 2010/0322878 A1 | 12/2010 | Stella et al. |
| 2010/0330018 A1 | 12/2010 | Lorant et al. |
| 2011/0053818 A1 | 3/2011 | Chuchotiros et al. |
| 2011/0065624 A1 | 3/2011 | Boutique et al. |
| 2011/0067720 A1 | 3/2011 | Ranade et al. |
| 2011/0070180 A1 | 3/2011 | Ranade et al. |
| 2011/0081392 A1 | 4/2011 | de Arruda et al. |
| 2011/0110991 A1 | 5/2011 | Garrison et al. |
| 2011/0248052 A1 | 10/2011 | Kelly et al. |
| 2012/0014900 A1* | 1/2012 | Carter ............... A61K 8/39 424/70.13 |
| 2012/0148644 A1 | 6/2012 | Popplewell et al. |
| 2012/0164198 A1 | 6/2012 | Johnson et al. |
| 2012/0308502 A1 | 12/2012 | Wise et al. |
| 2012/0329768 A1 | 12/2012 | Wise et al. |
| 2013/0029894 A1 | 1/2013 | Bettiol et al. |
| 2013/0090279 A1 | 4/2013 | Hilvert et al. |
| 2013/0131188 A1 | 5/2013 | Beckedahl et al. |
| 2013/0143784 A1 | 6/2013 | Rizk |
| 2013/0171216 A1 | 7/2013 | Alden-Danforth et al. |
| 2013/0174863 A1 | 7/2013 | Marsh et al. |
| 2013/0243717 A1 | 9/2013 | Catalan et al. |
| 2013/0243835 A1 | 9/2013 | Tanner et al. |
| 2014/0018276 A1 | 1/2014 | Coffindaffer et al. |
| 2014/0099276 A1 | 4/2014 | Operations |
| 2014/0112964 A1 | 4/2014 | Wu |
| 2014/0162931 A1 | 6/2014 | De Meirleir et al. |
| 2014/0199354 A1 | 7/2014 | Hilliard, Jr. et al. |
| 2014/0335041 A1 | 11/2014 | Peffly et al. |
| 2015/0010487 A1 | 1/2015 | Snyder et al. |
| 2015/0011450 A1 | 1/2015 | Carter et al. |
| 2015/0044157 A1 | 2/2015 | Kulkarni et al. |
| 2015/0059795 A1 | 3/2015 | Vatter et al. |
| 2015/0093422 A1 | 4/2015 | Garrison et al. |
| 2015/0102061 A1 | 4/2015 | Larson et al. |
| 2015/0313833 A1 | 11/2015 | Hilvert et al. |
| 2015/0342842 A1 | 12/2015 | Wise et al. |
| 2015/0374609 A1 | 12/2015 | Cetti et al. |
| 2016/0106663 A1 | 4/2016 | Gulbin |
| 2016/0143827 A1 | 5/2016 | Castan Barberan et al. |
| 2016/0256365 A1 | 9/2016 | Dihora et al. |
| 2017/0079306 A1 | 3/2017 | Ubbesen |
| 2017/0102720 A1 | 4/2017 | Goudy et al. |
| 2017/0216158 A1 | 8/2017 | Deckner et al. |
| 2017/0225183 A1 | 8/2017 | Kelly |
| 2017/0333734 A1 | 11/2017 | Mauer et al. |
| 2017/0367955 A1 | 12/2017 | Brown et al. |
| 2018/0071185 A1 | 3/2018 | Cochran et al. |
| 2018/0098923 A1 | 4/2018 | Hutton, III |
| 2018/0339845 A1 | 11/2018 | Moretti |
| 2018/0345538 A1 | 12/2018 | Smith et al. |
| 2018/0354767 A1 | 12/2018 | Cacciatore et al. |
| 2018/0354769 A1 | 12/2018 | Cacciatore et al. |
| 2018/0354770 A1 | 12/2018 | Cacciatore et al. |
| 2019/0105246 A1 | 4/2019 | Cochran et al. |
| 2019/0105247 A1 | 4/2019 | Song et al. |
| 2019/0201925 A1 | 7/2019 | Toh et al. |
| 2019/0290554 A1 | 9/2019 | Yokogi et al. |
| 2019/0290555 A1 | 9/2019 | Yokogi et al. |
| 2019/0290562 A1 | 9/2019 | Yokogi et al. |
| 2019/0290567 A1 | 9/2019 | Yokogi et al. |
| 2019/0290568 A1 | 9/2019 | Yokogi et al. |
| 2019/0307665 A1 | 10/2019 | Yokogi et al. |
| 2019/0345422 A1 | 11/2019 | Sunder et al. |
| 2019/0365611 A1 | 12/2019 | Brown et al. |
| 2020/0188243 A1 | 6/2020 | Brown et al. |
| 2021/0022975 A1 | 1/2021 | Cochran et al. |
| 2021/0045979 A1 | 2/2021 | Dunlop et al. |
| 2021/0253303 A1 | 8/2021 | Bartolucci et al. |

FOREIGN PATENT DOCUMENTS

| | | |
|---|---|---|
| CN | 1213294 A | 4/1999 |
| CN | 1568174 A | 1/2005 |
| CN | 1658825 A | 8/2005 |
| CN | 1658830 A | 8/2005 |
| CN | 101267797 A | 9/2008 |
| CN | 101965175 A | 2/2011 |
| CN | 102905682 A | 1/2013 |
| CN | 103458858 A | 12/2013 |
| CN | 105326670 A | 2/2016 |
| CN | 105395373 A | 3/2016 |
| CN | 105326660 B | 4/2018 |
| CN | 105395378 B | 7/2018 |
| DE | 19847968 A1 | 4/2000 |
| EP | 0037318 A1 | 10/1981 |
| EP | 0077630 A1 | 4/1983 |
| EP | 0627216 A2 | 12/1994 |
| EP | 1123693 A2 | 8/2001 |
| EP | 1066024 B1 | 10/2002 |
| EP | 1384467 B1 | 5/2007 |
| EP | 3075681 A1 | 10/2016 |
| FR | 2544890 A1 | 10/1984 |
| FR | 2593801 B1 | 5/1986 |
| FR | 1971709 A1 | 8/2012 |
| FR | 2984136 A1 | 6/2013 |
| GB | 849433 A1 | 9/1960 |
| GB | 1579131 A | 11/1980 |
| GB | 1582529 A | 1/1981 |
| GB | 2177108 B | 7/1989 |
| JP | 06134227 A | 5/1994 |
| JP | H07179887 A | 11/1994 |
| JP | H07118103 A | 5/1995 |
| JP | 07258039 A | 10/1995 |
| JP | 2001181145 A | 7/2001 |
| JP | 2002104940 A | 4/2002 |
| JP | 2003530446 A | 10/2003 |
| JP | 2004262805 A | 9/2004 |
| JP | 2004292387 A | 10/2004 |
| JP | 2004292390 A | 10/2004 |
| JP | 2004307463 A | 11/2004 |
| JP | 2005022983 A | 1/2005 |
| JP | 2005187342 A | 7/2005 |
| JP | 2005534644 A | 11/2005 |
| JP | 2006063044 A | 3/2006 |
| JP | 2006525232 A | 11/2006 |
| JP | 4016238 B2 | 9/2007 |
| JP | 2007527921 A | 10/2007 |
| JP | 4069228 B2 | 1/2008 |
| JP | 4129645 B2 | 5/2008 |
| JP | 2008524263 A | 7/2008 |
| JP | 2010504341 A | 2/2010 |
| JP | 2014231362 A | 12/2014 |
| JP | 2014533683 A | 12/2014 |
| JP | 2015512248 A | 4/2015 |

(56) References Cited

FOREIGN PATENT DOCUMENTS

| | | | |
|---|---|---|---|
| JP | 2016516674 A | 6/2016 | |
| WO | 9308787 A1 | 5/1993 | |
| WO | 9410973 A1 | 5/1994 | |
| WO | 9625913 A1 | 8/1996 | |
| WO | 9726854 A1 | 7/1997 | |
| WO | 9847372 A1 | 10/1998 | |
| WO | 9938489 A1 | 8/1999 | |
| WO | 9959540 A1 | 11/1999 | |
| WO | 0100149 A1 | 1/2001 | |
| WO | 0105932 A1 | 1/2001 | |
| WO | 0117492 A1 | 3/2001 | |
| WO | 0119946 A1 | 3/2001 | |
| WO | 0139735 A1 | 6/2001 | |
| WO | 02060995 A2 | 8/2002 | |
| WO | 02076422 A1 | 10/2002 | |
| WO | 2004020526 A1 | 3/2004 | |
| WO | 2004100919 A1 | 11/2004 | |
| WO | 2007031884 A1 | 3/2007 | |
| WO | 2009072027 A2 | 6/2009 | |
| WO | WO 2009/074465 | * | 6/2009 |
| WO | 2010006866 A1 | 1/2010 | |
| WO | 2010034736 A1 | 4/2010 | |
| WO | 2010111266 A2 | 9/2010 | |
| WO | 2011120799 A1 | 10/2011 | |
| WO | 2011134832 A2 | 11/2011 | |
| WO | 2012004126 A2 | 1/2012 | |
| WO | 2012138696 A2 | 10/2012 | |
| WO | 2012175677 A2 | 12/2012 | |
| WO | 20121756821 A2 | 12/2012 | |
| WO | 2013073849 A1 | 5/2013 | |
| WO | 2016040158 A1 | 3/2016 | |
| WO | 2016125167 A1 | 8/2016 | |
| WO | 2017088459 A1 | 6/2017 | |
| WO | 2018005453 A1 | 1/2018 | |
| WO | 2019236646 A1 | 12/2019 | |
| WO | 2020264569 A1 | 12/2020 | |
| WO | 2021163728 A1 | 8/2021 | |

OTHER PUBLICATIONS

All Office Actions; U.S. Appl. No. 18/174,082, filed on Feb. 24, 2023.
U.S. Appl. No. 18/174,082, filed on Feb. 24, 2023 to Mark Anthony Brown et al.
All Office Actions; U.S. Appl. No. 17/184,814, filed on Feb. 25, 2021.
"Herbal Essence Shampoo", Mintel, dated Jun. 1, 2014, 2 pages.
"Polyelectrolyte-Micelle—Coacervation—Effect of coacervate on the properties of shampoo", Yoshiko Kiwatari et al., J. Soc. Cosmet. Chem. Japan, vol. 38, No. 3, 2004, pp. 211-219.
1—Eccleston, G.M., Application of Emulsion Stability Theories to Mobile and Semisolid o/w Emulsions, Cosmetics Magazine, vol. 101, 1986, 18 pages.
14529 PCT Search Report and Written Opinion for PCT/US2017/055821 dated Dec. 6, 2017, 8 pages.
2—Eccleston, G.M., Application of Emulsion Theory to Complex and Real Systems, International Journal of Cosmetic Science, 1985, 18 pages.
3—Eccleston, G.M., Formulating Cosmetic Emulsions, Cosmetics Magazine, vol. 112, 1997, 6 pages.
4—Eccleston, G.M., Functions of Mixed Emulsifiers and Emulsifying Waxes in Dermatological Lotions and Creams, Colloids and Surfaces, vol. 123, 1997, 14 pages.
5—Eccleston, G.M., Microstructural Changes During Storage of Cetostearyl Alcohol/ Polyoxyethylene Alkyl Ether Surfactants, University of Strathclyde, 1988, 20 pages.
6—Eccleston, G.M., Multiple Phase Oil and Water Emulsions, Journal of Cosmetic Chemists, 1990, 22 pages.
7—Eccleston, G.M., Structure and Rheology of Semisolid o/w Creams Containing Cetyl Alcohol/Non-ionic Surfactant Mixed Emulsifier and Different Polymers, International Journal of Cosmetic Science, 2004, 7 pages.
8—Eccleston, G.M., Synchrotron X-ray Investigations into the Lamellar Gel Phase Formed in Creams Prepared with Fatty Alcohols, International Journal of Pharmaceuticals, 2000, 13 pages.
9—Eccleston, G.M., The Influence of Fatty Alcohols on the Structure and Stability of Creams Preapred with Fatty Alcohols, International Journal of Cosmetic Science, 1982, 9 pages.
All Office Actions; U.S. Appl. No. 16/907,711, filed on Jun. 22, 2020.
All Office Actions; U.S. Appl. No. 15/635,633, filed on Jun. 28, 2017.
All Office Actions; U.S. Appl. No. 15/703,046, filed on Sep. 13, 2017.
All Office Actions; U.S. Appl. No. 15/728,663, filed on Oct. 10, 2017.
All Office Actions; U.S. Appl. No. 16/713,142, filed on Dec. 13, 2019.
All Office Actions; U.S. Appl. No. 16/902,629, filed on Jun. 16, 2020.
All Office Actions; U.S. Appl. No. 16/432,371; filed on Jun. 5, 2019.
All Office Actions; U.S. Appl. No. 17/174,713, filed on Feb. 12, 2021.
All Office Actions; U.S. Appl. No. 17/174,427, filed on Feb. 12, 2021.
All Office Actions; U.S. Appl. No. 17/326,910, filed on May 21, 2021.
Barry & Rowe, The Characterization by Small Angle X-Ray Scattering of a Gel with a Lamellar Structure, International Journal of Pharmaceuticals, 1989, 2 pages.
Barry & Saunders, Kinetics of Structure Build-up in Self Bodied Emulsions Stabalized by Mixed Emulsifiers, Journal of Colloid Science, vol. 41, 1972, 12 pages.
Barry, B.W., Structure and Rheology of Emulsions Stabalized by Mixed Emulsifiers, British Society of Rheology, 1970, 12 pages.
Benton et al, Phase Behavior and Network Formation in a Cationic Surfactant-Fatty Alcohol System, Jaocs, vol. 64, 1987, 12 pages.
Burgess, J.D., Practical Analysis of Complex Coacervate Systems, Journal of Colloid Science, vol. 140, 1990, 10 pages.
CTFA Cosmetic Ingredient Dictionary, 1982, 3rd Edition, The Cosmetic, Toiletry & Fragrance Association, Inc., Washington, DC (book not included).
Database WPI Week 201634Thomson Scientific, London, GB;AN 2016-184949XP002798128,& CN 105 395 373 A (Cuongqing Pellets CoLtd) Mar. 16, 2016 (Mar. 16, 2016)abstract, 3 pages.
Database WPI Week 201644Thomson Scientific, London, GB;AN 2016-14284BXP002798127,& CN 105 326 660 A (Chongqing Pellets Colid) Feb. 17, 2016 (Feb. 17, 2016)abstract, 3 pages.
Encyclopedia of Polymer Science and Engineering, John Wiley & Sons, vol. 15, 1989 (book not included).
Griffin, W.C., Calculation of HLB Values of Non-Ionic Surfactants, Journal of the Society of Cosmetic Chemists; 1954. Vol. 5, pp. 249-235.
INCi: Ricinus Communis (Castor) Seed Oil, 3 pages, 2021.
Korhonen et al, Rheological Properties of Three Component Creams Containing Sorbitan Monoesters as Surfactants, International Journal of Pharmaceuticals, 2002, 2 pages.
Louden et al, A Preliminary Examination of the Structure of Gels and Emulsions Containing Cetostearyl Alcohol, International Journal of Pharmaceuticals, 1985, 2 pages.
McCutcheon, Emulsifiers and Detergents, MC Pub Company, 1989 (book not included).
Meirleir Niels De et al., "The rheological properties of hydrogenated castor oil crystals", Colloid & Polymer Science, Springer Verlag, Heidelberg, DE, vol. 292, No. 10, Jun. 12, 2014, pp. 2539-2547.
Momentive SFE839 product brochure, URL Link: https://www.momentive.com/products/showtechnicaldatasheet.aspx?id=14443, 4 pages. available Sep. 2008; accessed Jul. 17, 2015.
Noll, W., Chemistry and Technology of Silicones, Academic Press, 1968 (book not included).
Patel et al, Properties of Cetrimide / Cetostearyl Alcohol Ternary Gels; Preparation Effects, International Journal of Pharmaceuticals, 1985, 2 pages.

(56) References Cited

OTHER PUBLICATIONS

Savic et al, Colloidal Microstructure of Binary Systems and Model Creams Stablized with an Alkylpolyglucoside Emulsifier, Colloid Polymer Science, vol. 283, 2004, 13 pages.
Saxton, C., Antiplaque Effects and Mode of Action of a Combination of Zinc Citrate and a Nonionic Antimicrobial Agent, Scandinavian Journal, vol. 96, 1988, 7 pages.
Suzuki et al, Secondary Droplet Emulsion: Mechanism & Effects of Liquid Crystal Formation in o/w Emulsion, Journal of Dispersion Science, 1984, 24 pages.
U.S. Appl. No. 17/184,814, filed on Feb. 25, 2021, to Mark Anthony Brown et al.
U.S. Appl. No. 17/326,910, filed on May 21, 2021, to Howard David Hutton.
U.S. Appl. No. 17/174,713, filed on Feb. 12, 2021, to Mark Anthony Brown et al.
Van Cutsem, Journal of the American Academy of Dermatology, XP-002288119, 1998, 2 pages.
Van Oss, C.J., Coacervation, Complex Coacervation and Flocculation, Journal of Dispersion Science, vol. 9, 1989, 14 pages.
Yoon et al, A Study of Gel Structure in the Nonionic Surfactant / Cetostearyl Alcohol / Water Ternary Systems by Differential Scanning Calorimeter, Journal of Dispersion Science, Year 1999, 20 pages.

\* cited by examiner

PERSONAL CARE COMPOSITIONS SUBSTANTIALLY FREE OF SULFATED SURFACTANTS AND CONTAINING A GEL NETWORK

FIELD OF THE INVENTION

The present disclosure generally relates to personal care compositions substantially free of sulfated surfactants and which contain a dispersed gel network phase to provide cleaning benefits.

BACKGROUND OF THE INVENTION

Human hair becomes soiled due to contact with the surrounding environment and from sebum secreted by the scalp. Soiled hair has a dirty feel and exhibits an unattractive appearance. Application and washing of the soiled hair with a shampoo composition can restore hair to a clean and attractive appearance by removing oil and other soils from the hair. Known shampoo compositions typically remove oil and soil from hair through inclusion of sulfated surfactants. Shampoos including sulfated surfactants, such as sodium lauryl sulfate and sodium laureth sulfate, however, exhibit a number of undesirable characteristics such as poor quality hair feel as well as hair and skin dryness after washing due to the harshness of the sulfated surfactants. Shampoos including sulfated surfactants also face poor consumer acceptance as a consequence of this harshness. Consequently, it would be desirable to provide personal care compositions which can provide acceptable cleaning quality to soiled hair without exhibiting the harshness of shampoo compositions which include sulfated surfactants.

SUMMARY OF THE INVENTION

According to one embodiment, a personal care composition includes a dispersed gel network, a detersive surfactant, and a liquid carrier. The dispersed gel network includes about 0.05%, by weight of the personal care composition, of one or more fatty alcohols, and about 0.01% or more, by weight of the personal care composition, of a gel network surfactant, and water. The gel network surfactant is selected from a first group consisting of anionic surfactants, cationic surfactants, amphoteric surfactants, zwitterionic surfactants, non-ionic surfactants, and mixtures thereof. The detersive surfactant is selected from a second group consisting of anionic surfactants, cationic surfactants, amphoteric surfactants, zwitterionic surfactants, non-ionic surfactants, and mixtures thereof. The personal care composition is substantially free of sulfated surfactants.

According to another embodiment, a method of producing a personal care composition including combining one or more fatty alcohols and a gel network in a water solution at a temperature sufficient to allow partitioning of the gel network surfactant into the one or more fatty alcohols to form a mixture, cooling the mixture to a temperature below the chain melt temperature of the one or more fatty alcohols to form a gel network, and adding the gel network to a detersive surfactant and a liquid carrier to form a personal care composition. The one or more fatty alcohols and the gel network surfactant are combined in a weight ratio of about 1:1 to about 40:1. The personal care composition is substantially free of sulfated surfactants.

According to another embodiment, a method of cleaning a substrate without sulfates includes providing a personal care composition, forming a lather with water and the personal care composition to clean the substrate, and rinsing the lather out of the substrate. The personal care composition includes a dispersed gel network, a detersive surfactant, and a liquid carrier. The dispersed gel network includes about 0.05%, by weight of the personal care composition, of one or more fatty alcohols, about 0.01% or more, by weight of the personal care composition, of a gel network surfactant, and water. The gel network surfactant is selected from a first group consisting of anionic surfactants, cationic surfactants, amphoteric surfactants, zwitterionic surfactants, non-ionic surfactants, and mixtures thereof. The detersive surfactant is selected from a second group consisting of anionic surfactants, cationic surfactants, amphoteric surfactants, zwitterionic surfactants, non-ionic surfactants, and mixtures thereof. The personal care composition is substantially free of sulfated surfactants.

BRIEF DESCRIPTION OF THE DRAWINGS

FIG. 1 is a picture depicting four hair samples and demonstrating the relative cleaning benefit provided by various personal care compositions.

DETAILED DESCRIPTION OF THE INVENTION

While the specification concludes with claims which particularly point out and distinctly claim the invention, it is believed the present disclosure will be better understood from the following description.

Definitions

In all embodiments of the present disclosure, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at about 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "charge density," as used herein, refers to the ratio of the number of positive charges on a polymer to the molecular weight of said polymer.

The term "comprising," as used herein, means that other steps and other ingredients which do not affect the end result can be added. This term encompasses the terms "consisting of" and "consisting essentially of." The compositions and methods/processes of the present disclosure can comprise, consist of, and consist essentially of the elements and limitations of the invention described herein, as well as any of the additional or optional ingredients, components, steps, or limitations described herein.

The term "polymer," as used herein, includes materials whether made by polymerization of one type of monomer or made by two (i.e., copolymers) or more types of monomers.

The term "suitable for application to human hair," as used herein, means that the personal care compositions or components thereof, are acceptable for use in contact with human hair and the scalp and skin without undue toxicity, incompatibility, instability, allergic response, and the like.

The term "water soluble," as used herein, means that the material is soluble in water. In certain embodiments, the material can be soluble at 25° C. at a concentration of 0.1% by weight of the water solvent, in certain embodiments at 1% by weight of the water solvent, in certain embodiments at 5% by weight of the water solvent, and in certain embodiments at 15% or more by weight of the water solvent.

The terms "sulfate free" and "substantially free of sulfates" means essentially free of sulfate-containing compounds except as otherwise incidentally incorporated as minor components.

The term "sulfated surfactants" means surfactants which contain a sulfate group. The term "substantially free of sulfated surfactants" means essentially free of surfactants containing a sulfate group except as otherwise incidentally incorporated as minor components.

Personal Care Compositions

As will be described herein, a personal care composition is disclosed which exhibits excellent cleaning qualities without the use, or inclusion, of a sulfated surfactant. Generally, the personal care compositions described herein can alternatively include a dispersed gel network phase which provides a milder, but effective, cleaning benefit to soiled hair in combination with a detersive surfactant substantially free of sulfates. According to certain embodiments, the personal care compositions described herein can be free of sulfated surfactants and can include a detersive surfactant, a dispersed gel network phase, and a liquid carrier. In certain embodiments, a personal care composition can also entirely be substantially free of sulfates.

Detersive Surfactant

According to certain embodiments, the personal care compositions described herein can include one or more detersive surfactants. As can be appreciated, surfactants provide a cleaning benefit to soiled hair and hair follicles by facilitating the removal of oil and other soil components from the soiled hair. Surfactants generally facilitate such cleaning due to their amphiphilic nature which allows for the surfactants to break up, and form micelles around, oil and other soils in the hair which can then be rinsed out, thereby removing them from the hair.

Traditional shampoo compositions generally include sulfated surfactants such as sodium lauryl sulfate, sodium laureth sulfate, ammonium lauryl sulfate, and ammonium laureth sulfate to provide a cleaning benefit. Although sulfated surfactants are effective at removing oil and other soils from hair and skin surfaces of a consumer, such sulfated surfactants also remove beneficial oils. Hairs and skins washed with such sulfated surfactants can be unattractive and can have a dry feel to consumers. The personal care compositions described herein can be substantially free of any sulfated surfactants and can alternatively include milder detersive surfactants. As used herein, "detersive surfactant" means a surfactant substantially free of sulfates.

According to certain embodiments, suitable detersive surfactants can instead be selected from one or more anionic surfactants, cationic surfactants, amphoteric surfactants, zwitterionic surfactants, and non-ionic surfactants which are substantially free of sulfates. Such surfactants should generally be physically and chemically compatible with the other components of the personal care compositions described herein and should not otherwise unduly impair product stability, aesthetics, or performance.

A. Anionic Surfactants

Examples of suitable anionic detersive surfactants for use in the personal care compositions described herein can include those which are known for use in hair care or other personal care compositions including, for example, isethionate, sarcosinate, sulfonate, sulfosuccinate, sulfoacetate, glycinate, glutamate, glucosecarboxylate, and phosphate ester surfactants.

In certain embodiments, suitable anionic surfactants can include water-soluble olefin sulfonates which have the general formula $R^1$—$SO_3M$ where $R^1$ is a straight or branched chain, saturated, aliphatic hydrocarbon radical having from 10 to 24 carbon atoms, 10 to 18 carbon atoms, or from 13 to 15 carbon atoms; and M is a water soluble cation such as ammonium, sodium, potassium, triethanolamine cation, or salts of the divalent magnesium ion with two anionic surfactant anions. Suitable olefin sulfonates such as sodium paraffin sulfonates can be produced through the reaction of $SO_2$ and $O_2$ with a suitable chain length paraffin.

In certain embodiments, suitable olefin sulfonates can also contain minor amounts of other materials, such as alkene disulfonates depending upon the reaction conditions, proportion of reactants, the nature of the starting olefins and impurities in the olefin stock and side reactions during the sulfonation process. Examples of additional olefin sulfonates and mixtures thereof are described in U.S. Pat. No. 3,332,880, which is incorporated herein by reference.

Another class of suitable anionic detersive surfactants includes the beta-alkyloxy alkane sulfonates. Beta-alkyloxy alkane sulfonates surfactants conform to Formula I:

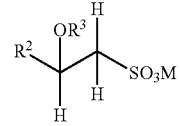

Formula I where $R^2$ is a straight chain alkyl group having from about 6 to about 20 carbon atoms, $R^3$ is a lower alkyl group having from about 1 to about 3 carbon atoms, preferably 1 carbon atom, and M is a water-soluble cation as previously described in the water-soluble olefin sulfonates.

In certain embodiments, suitable anionic detersive surfactants can include isethionate surfactants. For example, suitable isethionate surfactants can include the reaction product of fatty acids esterified with isethionic acid and neutralized with sodium hydroxide. In certain embodiments, suitable fatty acids for isethionate surfactants can be derived from coconut oil or palm kernel oil including amides of methyl tauride. Additional examples of suitable isethionic anionic surfactants are described in U.S. Pat. Nos. 2,486,921; 2,486,922; and 2,396,278, each of which is incorporated herein by reference.

In certain embodiments, detersive anionic surfactants can be succinate surfactants. Examples of suitable succinate surfactants can include disodium N-octadecylsulfo succinnate, disodium lauryl sulfosuccinate, diammonium lauryl sulfosuccinate, laureth sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid.

In certain embodiments, suitable anionic detersive surfactants can include one or more of sodium cocoyl isethionate ("SCI"), sodium lauroyl methyl isethionate ("SLMI"), sodium lauroyl sarcosinate, sodium $C_{12}$-$C_{14}$ olefin sulfonate, sodium lauroyl glycinate, sodium cocoamphoacetate, sodium cocoyl glutamate, sodium lauryl glucosecarboxylate, sodium lauryl sulfosuccinate, sodium laureth sulfosuccinate, sodium lauryl sulfoacetate, lauryl sarcosine, cocoyl sarcosine, sodium methyl lauroyl taurate, sodium methyl lauroyl taurate, sodium tridecyl benzene sulfonate, sodium dodecyl benzene sulfonate, phosphate ester surfactants, and fatty acid surfactants.

B. Cationic Surfactants

In certain embodiments, a suitable detersive surfactant can be a cationic surfactant described by Formula II:

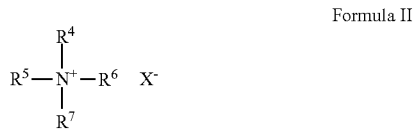

Formula II wherein at least one of $R^4$, $R^5$, $R^6$ and $R^7$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, and wherein the remainder of $R^4$, $R^5$, $R^6$ and $R^7$ are independently selected from an aliphatic group having from 1 to 22 carbon atoms or an aromatic, alkoxy, polyoxyalkylene, alkylamido, hydroxyalkyl, aryl or alkylaryl group having up to 22 carbon atoms; and $X^-$ is a salt-forming anion such as a halogen (e.g. chloride, bromide), acetate, citrate, lactate, glycolate, phosphate, nitrate, sulfonate, alkylsulfate, and alkyl sulfonate radicals. The aliphatic groups can contain, in addition to carbon and hydrogen atoms, ether linkages, and other groups such as amino groups. The longer chain aliphatic groups, e.g., those of 12 carbon atoms, or higher, can be saturated or unsaturated. In certain embodiments, $R^4$, $R^5$, $R^6$ and $R^7$ are independently selected from $C_1$ to $C_{22}$ branched or straight alkyl or alkenyl groups. Specific examples of cationic surfactants can include compounds having the following Cosmetic, Toiletries, and Fragrance Association ("CTFA") designations: quaternium-8, quaternium-14, quaternium-18, quaternium-18 methosulfate, quaternium-24, and mixtures thereof.

In certain embodiments, suitable cationic surfactants of Formula II can include at least one alkyl chain having at least 16 carbon atoms. Examples of such surfactants can include: behenyl trimethyl ammonium chloride available, for example, with tradename INCROQUAT TMC-80 from Croda and ECONOL TM22 from Sanyo Kasei; cetyl trimethyl ammonium chloride available, for example, with tradename CA-2350 from Nikko Chemicals, hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

In certain embodiments, a primary, secondary, or tertiary fatty amine cationic surfactant can be selected. Particularly useful are tertiary amido amines having an alkyl group including 12 to 22 carbon atoms. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethyl amine, behenamidopropyldiethylamine, behenamidoethyldiethyl amine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with about 5 moles of ethylene oxide) stearylamine, dihydroxyethylstearylamine, isostearylamidopropyldimethylamine, oleamidopropyldimethylamine, cocamidopropyldimethylamine and arachidylbehenylamine.

In certain embodiments, suitable cationic amine surfactants can include bis-hydroxyethyl lauryl amine, lauryl dimethylamine, lauroyl dimethyl amidoproplyl amine, cocoylamidopropyl amine, and the like. Additional amine surfactants are disclosed in U.S. Pat. No. 4,275,055 which is incorporated by reference herein.

In certain embodiments, amines can be used in combination with acids such as ℓ-glutamic acid, lactic acid, hydrochloric acid, malic acid, succinic acid, acetic acid, fumaric acid, tartaric acid, citric acid, maleic acid, and mixtures thereof. In such embodiments, the amine can be partially neutralized with such acids at a molar ratio of the amine to the acid of from about 1:0.3 to about 1:3 in certain embodiments, and a ratio of from about 1:0.4 to about 1:2 in certain embodiments. In certain embodiments, the acid can be ℓ-glutamic acid, lactic acid, or citric acid.

In certain embodiments including a cationic surfactant, it can be beneficial to include a tertiary amine or quaternary amine. For example, in certain embodiments, suitable cationic surfactants can be a mono-alkyl or alkenyl amidoamine, a mono-alkyl or alkenyl ammonium salt, a di-alkyl ammonium salt, a PEG(n) alkylamine, or any combination thereof. The cationic alkyl or alkenyl chain length can be between 10 and 40 carbon atoms and can be branched or straight. In certain embodiments, the alkyl or alkenyl chain length can be 12 to 22 carbon atoms long. In certain embodiments, the alkyl or alkenyl chain length can be between 16 and 18 carbon atoms long.

In certain embodiments, a suitable cationic detersive surfactant can be selected from the group consisting of cetrimonium chloride, stearimonium chloride, behentrimonium chloride, behentrimonium methosulfate, behenamidopropyltrimonium methosulfate, stearamidopropyltrimonium chloride, arachidtrimonium chloride, and distearyldimonium chloride.

C. Amphoteric Surfactants

In certain embodiments, a personal care composition can include a suitable amphoteric detersive surfactant. Generally any sulfate-free amphoteric surfactant known for use in hair care or other personal care compositions can be suitable. For example, amphoteric detersive surfactants suitable for inclusion in a personal care composition described herein can include those surfactants broadly described as derivatives of aliphatic secondary and tertiary amines in which the aliphatic radical can be straight or branched chain and wherein one of the aliphatic substituents contains from 8 to 18 carbon atoms and one aliphatic substituent contains an anionic group such as a carboxy, sulfonate, phosphate, or phosphonate group. In certain embodiments, suitable amphoteric detersive surfactants can include cocoamphoacetate, cocoamphodiacetate, lauroamphoacetate, lauroamphodiacetate, and mixtures thereof. Other suitable amphoteric surfactants include amidobetaines and amidosulfobetaines.

D. Zwitterionic Surfactants

A personal care composition can, in certain embodiments, include a suitable zwitterionic detersive surfactant. For example, in certain embodiments, a personal care composition can include surfactants broadly described as derivatives of aliphatic quaternary ammonium, phosphonium, and sulfonium compounds, in which the aliphatic radicals can be straight or branched chain, and wherein one of the aliphatic substituents contains from 8 to 18 carbon atoms and one aliphatic substituent contains an anionic group such as carboxy, sulfonate, phosphate or phosphonate group. In certain embodiments, betaine zwitterionic surfactants, including high alkyl betaines, can be beneficial. In certain embodiments, a zwitterionic surfactant can alternatively, or additionally, be a sultaine surfactant. For example, hydroxysultaine surfactants such as cocamidopropyl hydroxysultaine can also be suitable.

Examples of betaine zwitterionic surfactants can include coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

E. Non-Ionic Surfactants

In certain embodiments, a personal care composition can include a nonionic detersive surfactant. Generally, suitable nonionic surfactants can include compounds produced by the condensation of alkylene oxide groups (hydrophilic in nature) with an organic hydrophobic compound, which may be aliphatic or alkyl aromatic in nature. Examples of suitable nonionic detersive surfactants can include:

1. The polyethylene oxide condensates of alkyl phenols. For example, the condensation products of alkyl phenols having an alkyl group containing from 6 to 20 carbon atoms in either a straight chain or branched chain configuration, with ethylene oxide, the said ethylene oxide being present in amounts equal to from about 10 to about 60 moles of ethylene oxide per mole of alkyl phenol.
2. Those derived from the condensation of ethylene oxide with the product resulting from the reaction of propylene oxide and ethylene diamine products.
3. The condensation product of aliphatic alcohols having from 8 to 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from 10 to 14 carbon atoms.
4. Long chain tertiary amine oxides corresponding to the following general formula:

$R^8R^9R^{10}N \rightarrow O$ wherein $R^8$ contains an alkyl, alkenyl or monohydroxy alkyl radical of from 8 to 18 carbon atoms, from 0 to about 10 ethylene oxide moieties, and from 0 to about 1 glyceryl moieties, and $R^9$ and $R^{10}$ contain from 1 to 3 carbon atoms and from 0 to about 1 hydroxy groups, e.g., methyl, ethyl, propyl, hydroxyethyl, or hydroxypropyl radicals. The arrow in the formula is a conventional representation of a semipolar bond.
5. Long chain tertiary phosphine oxides corresponding to the following general formula:

$R^{11}R^{12}R^{13}P \rightarrow O$ wherein $R^{11}$ contains an alkyl, alkenyl or monohydroxyalkyl radical ranging from 8 to 18 carbon atoms in chain length, from 0 to about 10 ethylene oxide moieties and from 0 to about 1 glyceryl moieties and $R^{12}$ and $R^{13}$ are each alkyl or monohydroxyalkyl groups containing from 1 to 3 carbon atoms.
6. Long chain dialkyl sulfoxides containing one short chain alkyl or hydroxy alkyl radical of from 1 to 3 carbon atoms (usually methyl) and one long hydrophobic chain which include alkyl, alkenyl, hydroxy alkyl, or keto alkyl radicals containing from 8 to 20 carbon atoms, from 0 to about 10 ethylene oxide moieties and from 0 to about 1 glyceryl moiety.
7. Alkyl polysaccharide ("APS") surfactants such as the alkyl polyglycosides. Such surfactants are described in U.S. Pat. No. 4,565,647 which is hereby incorporated by reference. APS surfactants can include a hydrophobic group with 6 to 30 carbon atoms and can include polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).
8. Polyethylene glycol (PEG) glyceryl fatty esters, such as those of the formula $R(O)OCH_2CH(OH)CH_2(OCH_2CH_2)_nOH$ wherein n is from 5 to 200 or from 20 to 100, and R is an aliphatic hydrocarbyl having from 8 to 20 carbon atoms.
9. Glucoside surfactants including, for example, lauryl glucoside, coco glucoside, and decyl glucoside.
10. Certain surfactant-emulsifying compounds such as laureth-4.

In certain embodiments, specific examples of non-ionic detersive surfactants suitable for inclusion in a personal care composition can include cocamide, cocamide methyl MEA, cocamide DEA, cocamide MEA, cocamide MIPA, lauramide DEA, lauramide MEA, lauramide MIPA, myristamide DEA, myristamide MEA, PEG-20 cocamide MEA, PEG-2 cocamide, PEG-3 cocamide, PEG-4 cocamide, PEG-5 cocamide, PEG-6 cocamide, PEG-7 cocamide, PEG-3 lauramide, PEG-5 lauramide, PEG-3 oleamide, PPG-2 cocamide, PPG-2 hydroxyethyl cocamide, and mixtures thereof.

Additional examples of suitable detersive surfactants are described in McCutcheon's, Emulsifiers and Detergents, 1989 Annual, published by M. C. Publishing Co., U.S. Pat. Nos. 2,438,091, 2,528,378, 2,658,072, 3,929,678, 5,104,646, and 5,106,609, 6,649,155; U.S. Patent Application Publication No. 2008/0317698; and U.S. Patent Application Publication No. 2008/0206355, each of which are incorporated herein by reference.

The concentration of detersive surfactants in the personal care compositions can generally be selected to provide the desired cleaning and lather performance to the composition in combination with a dispersed gel network phase. In certain embodiments, a personal care composition can include, by weight, about 5% to about 50% of a detersive surfactant, in certain embodiments about 8% to about 30% of a detersive surfactant, in certain embodiments about 9% to about 25% of a detersive surfactant, and in certain embodiments about 10% to about 17% of a detersive surfactant.

Dispersed Gel Network Phase

The personal care compositions described herein can include a dispersed gel network phase to provide a suitable cleaning benefit to the composition in combination with the detersive surfactant. As used herein, the term "gel network phase" or "dispersed gel network phase" refers to a lamellar or vesicular solid crystalline phase which includes at least one fatty alcohol, at least one gel network surfactant, and a liquid carrier. The lamellar or vesicular phase can be formed of alternating layers with one layer including the fatty alcohol and the gel network surfactant and the other layer formed of the liquid carrier.

As used herein, the term "solid crystalline" refers to the crystalline structure of the lamellar or vesicular phase at ambient temperatures caused by the phase being below its melt transition temperature. In certain embodiments, the melt transition temperature of the lamellar or vesicular phase can be about 30° C. or more (i.e., slightly above about room temperature). As can be appreciated, the melt transition temperature can be measured through differential scanning calorimetry.

Suitable dispersed gel networks can be formed by combining a fatty alcohol and a gel network surfactant in a suitable ratio and heating the dispersion to a temperature above the melting point of the fatty alcohol. During the mixing process, the fatty alcohol melts allowing the gel network surfactant to partition and bring water into the fatty alcohol. Mixing of the gel network surfactant and fatty alcohols also changes the isotropic fatty alcohol drops into liquid crystalline phase drops. When the mixture is subsequently cooled below the melt transition temperature of the fatty alcohols, the liquid crystal phase is converted into a solid crystalline gel network.

Additional details of suitable gel networks are described in G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International*, Vol. 7, 63-70 (1986), each of which is incorporated by reference herein.

Applicant has unexpectedly discovered that a gel network phase can provide a previously unknown cleaning benefit when included in a personal care composition substantially free of sulfated surfactants. Without being bound by theory, Applicant believes that the gel network phase confers a cleaning benefit to the personal care composition through its hydrophobic nature. Specifically, it is theorized that the hydrophobic nature of the dispersed gel network allows the gel network to dissolve hydrophobic soils such as oil into the gel network. Once the soils are dissolved into the gel network, the gel network can be rinsed out of the hair or skin.

In certain embodiments, a gel network phase can be pre-formed. The term "pre-formed", as used herein, means that at least fifty percent of the mixture of the fatty alcohol, gel network surfactant, and liquid carrier are in a substantially solid crystalline phase prior to addition to the other components of a personal care composition.

In embodiments where a dispersed gel network is pre-formed, the gel network component can be prepared as a separate pre-mix, which, after being cooled, can be subsequently incorporated with a detersive surfactant and any other components of a personal care composition. Additional details discussing the formation of a pre-mixed dispersed gel network are explained in further detail herein in the section entitled Process of Making a Personal Care Composition as well as in the Examples.

While not intending to be limited by theory, it is believed that incorporation of a pre-formed gel network component with the detersive surfactant and other components of the personal care composition allows the formation of a substantially equilibrated lamellar dispersion ("ELD") in the final composition. The ELD is a dispersed lamellar or vesicular phase resulting from the pre-formed gel network component substantially equilibrating with the detersive surfactants, carrier, and other optional components of a personal care composition. This equilibration occurs upon incorporation of the pre-formed gel network component with the other components of a personal care composition and can be effectively complete within about 24 hours after incorporation. The ELD does not form if the components which comprise the gel network component (i.e., the fatty alcohol, the gel network surfactant, and the liquid carrier) are added as individual components together with the other components of the personal care composition in one mixing step, and not as a separate pre-formed gel network component.

The presence of a gel network in the pre-mix and in a personal care composition can be confirmed by means known to one of skill in the art. For example, X-ray analysis, optical microscopy, electron microscopy, and differential scanning calorimetry can be used to identify a gel network. A suitable x-ray analysis is described in U.S. Patent App. Publication No. 2006/0024256 which is hereby incorporated by reference.

According to certain embodiments, the scale size of the dispersed gel network in a personal care composition can range from about 10 nm to about 500 nm. In certain embodiments, the scale size of the dispersed gel network in a personal care composition can range from about 0.5 μm to about 10 μm. In other certain embodiments, the scale size of a dispersed gel network in a personal care composition can range from about 10 μm to about 150 μm.

The scale size distribution of the dispersed gel network in a personal care composition can be measured with a laser light scattering technique using a Horiba model LA 910 Laser Scattering Particle Size Distribution Analyzer (Horiba Instruments, Inc. Irvine California, USA). The scale size distribution in a personal care composition can be measured by combining 1.75 g of the personal care composition with 30 mL of 3% $NH_4Cl$, 20 mL of 2% $Na_2HPO_4 \cdot 7H_2O$, and 10 mL of 1% laureth-7 to form a mixture. This mixture is then stirred for 5 minutes. As appropriate for the individual Horiba instrument being used, samples in the range of 1 to 40 mL are taken and then injected into the Horiba instrument, which contains 75 mL of 3% $NH_4Cl$, 50 mL of 2% $Na_2HPO_4 \cdot 7H_2O$, and 25 mL of 1% laureth-7, until the Horiba instrument reading is between 88-92% T, which is needed for the scale size measurement. Once this is achieved, a measurement is taken after 2 minutes of circulation through the Horiba instrument to provide the scale size measurement. A subsequent measurement is taken using a sample of the personal care composition which has been heated above the melt transition temperature of all fatty materials present in the shampoo composition to ensure the dispersed gel network is melted. This subsequent measurement allows a scale size distribution to be taken of all of the remaining materials in the personal care composition, which can then be compared to the scale size distribution of the first sample and assist in the analysis.

A. Fatty Alcohol of the Gel Network Phase

A dispersed gel network can include at least one fatty alcohol. Individual fatty alcohol compounds or combinations of two or more different fatty alcohol compounds can be selected in certain embodiments.

Suitable fatty alcohols can include fatty alcohols having from about 10 to about 40 carbon atoms in certain embodiments, from about 12 to about 30 carbon atoms in certain embodiments, from about 14 to about 22 carbon atoms in certain embodiments, and from about 16 to about 18 carbon atoms in certain embodiments. Suitable fatty alcohols can be straight or branched chain alcohols and can be saturated or unsaturated. Non-limiting examples of suitable fatty alcohols include cetyl alcohol, stearyl alcohol, arachidyl alcohol, behenyl alcohol, $C_{21}$ fatty alcohol (1-heneicosanol), $C_{23}$ fatty alcohol (1-tricosanol), $C_{24}$ fatty alcohol (lignoceryl alcohol, 1-tetracosanol), $C_{26}$ fatty alcohol (1-hexacosanol), $C_{28}$ fatty alcohol (1-octacosanol), $C_{30}$ fatty alcohol (1-triacontanol), $C_{20-40}$ alcohols (e.g., Performacol® 350 and 425 Alcohols, available from New Phase Technologies), $C_{30-50}$ alcohols (e.g., Performacol® 550 Alcohol), $C_{40-60}$ alcohols (e.g., Performacol® 700 Alcohol), and mixtures thereof. As can be appreciated, suitable fatty alcohols can be of natural, vegetable, or synthetic origin.

In certain embodiments, a mixture of several fatty alcohols can be suitable. For example, a suitable mixture can include one or more fatty alcohols having from about 10 to about 40 carbon atoms as well as other fatty alcohols and amphiphiles which have 18 carbon atoms or less. Mixtures of several fatty alcohols are suitable if the resulting dispersed gel network phase has a melt transition temperature of about 38° C. or greater. For example, mixtures of cetyl alcohol and stearyl alcohol in a ratio of from about 20:80 to a ratio of from about 80:20 can be suitable.

In certain embodiments, a fatty alcohol can be included by weight of the personal care composition. For example, in certain embodiments, a fatty alcohol can be included at 0.05% or more, by weight, in certain embodiments at about 0.05% to about 25% by weight, in certain embodiments at about 0.5% to about 20% by weight, and in certain embodiments at about 1% to about 8% by weight.

B. Gel Network Surfactant

The gel network phase of the personal care compositions described herein can include a gel network surfactant. As used herein, "gel network surfactant" refers to one or more surfactants which can be combined with the fatty alcohol and liquid carrier to form a gel network as a pre-mix separate from the other components of a personal care composition.

Suitable gel network surfactants can include any anionic, zwitterionic, amphoteric, cationic, and nonionic surfactants substantially free of sulfates, including any of the surfactants suitable for the detersive surfactant of the personal care composition. In such embodiments, the detersive surfactant and the gel network surfactant can each be independently selected and can be the same or different in certain embodiments.

In certain embodiments, a suitable gel network surfactant can have a hydrophobic tail group with a chain length of from about 10 to about 40 carbon atoms. For such gel network surfactants, the hydrophobic tail group can be alkyl, alkenyl (containing up to 3 double bonds), alkyl aromatic, or branched alkyl. As can be appreciated, mixtures of more than one gel network surfactant can also be used. Additional gel network surfactants are disclosed in U.S. Patent App. Pub. No. 2006/0024256 which is hereby incorporated by reference.

In certain embodiments, a gel network surfactant can be included in a gel network at about 0.01% to about 15% by weight of a personal care composition, alternatively from about 0.1% to about 10% by weight of a personal care composition, and alternatively from about 0.2% to about 5%, by weight of a personal care composition. In certain embodiments, the total weight of the gel network surfactant and the fatty alcohols can be about 0.5% to about 15%, by weight, of the personal care composition. In certain embodiments, the total weight of the gel network surfactant and the fatty alcohols can be about 1% to about 10%, by weight, of the personal care compositions.

Alternatively, a gel network surfactant can be included in the gel network at desired weight ratios with respect to the fatty alcohols. In such embodiments, the ratio of the fatty alcohols to the gel network surfactant can be about 1:5 to about 100:1 in certain embodiments, about 1:1 to about 40:1 in certain embodiments, about 2:1 to about 20:1 in certain embodiments, and about 3:1 to about 10:1 in certain embodiments.

C. Liquid Carrier for the Gel Network Phase

A dispersed gel network phase further includes a suitable liquid carrier. In certain embodiments, the liquid carrier can be water or another suitable solvent. The water or other suitable solvent and the gel network surfactant combine to contribute to the swelling of the fatty alcohol. This swelling leads to the formation and the stability of a gel network phase. As used herein, the term "suitable solvent" refers to any solvent which can be used in the place of or in combination with water in the formation of the gel network phase. In certain embodiments however, the liquid carrier can be substantially free of solvents other than water.

The dispersed gel network phase can include a liquid carrier in an amount suitable to achieve a gel network when combined with fatty alcohol and a gel network surfactant. For example, in certain embodiments, about 0.05% to about 95% by weight of the personal care composition can be the liquid carrier of the dispersed gel network. In other certain embodiments, the liquid carrier for the dispersed gel network phase can be included at a weight ratio of about 1:1 with the fatty alcohol of the dispersed gel network phase.

Liquid Carrier for the Personal Care Composition

The personal care composition also includes a liquid carrier separate from the liquid carrier of the dispersed gel network phase. Inclusion of an appropriate quantity of a liquid carrier can facilitate the formation of a personal care composition having an appropriate viscosity and rheology. A personal care composition can include, by weight of the composition, about 20% to about 95% of a liquid carrier in certain embodiments, and about 60% to about 85% of a liquid carrier in certain embodiments.

A liquid carrier can be water, or can be a miscible mixture of water and organic solvent. In certain embodiments however, a liquid carrier can be water with minimal or no significant concentrations of organic solvent, except as otherwise incidentally incorporated into the composition as minor ingredients of other essential or optional components. Suitable organic solvents can include water solutions of lower alkyl alcohols and polyhydric alcohols. Useful lower alkyl alcohols include monohydric alcohols having 1 to 6 carbons, such as ethanol and isopropanol. Exemplary polyhydric alcohols include propylene glycol, hexylene glycol, glycerin, and propane diol.

Optional Components

As can be appreciated, personal care compositions described herein can include a variety of optional components to tailor the properties and characteristics of the composition. As can be appreciated, suitable optional components are well known and can generally include any components which are physically and chemically compatible with the essential components of the personal care compositions described herein. Optional components should not otherwise unduly impair product stability, aesthetics, or performance Individual concentrations of optional components can generally range from about 0.001% to about 10%, by weight of a personal care composition.

In certain embodiments, examples of optional components which can be included in a personal care composition can include co-surfactants, deposition aids, cationic polymers, conditioning agents (including hydrocarbon oils, fatty esters, silicones), anti-dandruff agents, suspending agents, viscosity modifiers, dyes, nonvolatile solvents or diluents (water soluble and insoluble), pearlescent aids, foam boosters, pediculocides, pH adjusting agents, perfumes, preservatives, chelants, proteins, skin active agents, sunscreens, UV absorbers, and vitamins Co-Surfactants In certain embodiments, one or more co-surfactants can be included in a personal care composition to enhance various properties of a personal care composition. For example, a co-surfactant can improve the production of lather, facilitate easier rinsing, or further mitigate the harshness on detersive surfactants on keratinous tissue. In certain embodiments, a co-surfactant further can also aid in producing lather having more desirable textures and volume. In embodiments including co-surfactants, suitable co-surfactants can be selected from any of the sulfate-free amphoteric, zwitterionic, cationic, and nonionic surfactants previously disclosed as suitable detersive surfactants. When included, a co-surfactant can be included in a ratio with the detersive surfactant. For example, the ratio of the detersive surfactant to a co-surfactant can be about 1:20 to about 1:4 in certain embodiments, and a ratio of about 1:12 to about 1:7 in certain embodiments.

Alternatively, a co-surfactant can be included by weight percentage of the personal care composition. For example, a personal care composition can include a co-surfactant by weight of about 0.5% to about 10%, about 0.5% to about 5%, about 0.5% to about 3%, about 0.5% to about 2%, and about 0.5% to about 1.75%.

Deposition Aid

In certain embodiments, a personal care composition can include a deposition aid to enhance deposition of the dispersed gel network phase. When included, a deposition aid can generally be selected from any material that enhances deposition of the gel network onto the hair and/or scalp. A deposition aid can be included at a concentration sufficient to effectively enhance the deposition of the gel network phase. In certain embodiments, a deposition aid can be included from about 0.05% to about 5% by weight, in certain embodiments, from about 0.075% to about 2.5% by weight, and in certain embodiments, from 0.1% to about 1.0%, by weight of the personal care composition. In certain embodiments, a deposition aid can be a cationic polymer.

Cationic Polymers

In certain embodiments, a personal care composition can include a cationic polymer. A cationic polymer can be used to increase deposition of the dispersed gel network phase or aid in the formation of a coacervate. In embodiments including a cationic polymer, the polymer can be included by weight of the personal care composition at about 0.05% to about 3%, about 0.075% to about 2.0%, or at about 0.1% to about 1.0%. In certain embodiments, cationic polymers can have cationic charge densities of about 0.9 meq/gm or more, about 1.2 meq/gm or more, and about 1.5 meq/gm or more. However, cationic charge density can also be about 7 meq/gm or less in certain embodiments and about 5 meq/gm or less in certain embodiments. The charge densities can be measured at the pH of intended use of the personal care composition. (e.g., at about pH 3 to about pH 9; or about pH 4 to about pH 8). In certain embodiments, the average molecular weight of cationic polymers can generally be between about 10,000 and 10 million, between about 50,000 and about 5 million, and between about 100,000 and about 3 million.

In certain embodiments, suitable cationic polymers can contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Anionic counterions can be used in association with the cationic polymers so long as the polymers remain soluble in water, in the composition, and in a coacervate phase of the composition. Examples of suitable counterions include halide counterions (e.g., chloride, fluoride, bromide, iodide).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers can include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers can include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). In certain embodiments, suitable cationic substituted monomers include cationic substituted dialkylaminoalkyl acrylamides, dialkylaminoalkyl methacrylamides, and combinations thereof. Generally, cationic monomers can conform to the formula III:

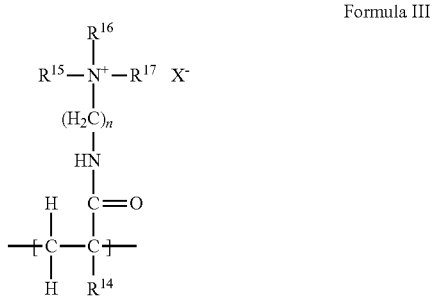

Formula III wherein $R^{14}$ is hydrogen, methyl or ethyl; each of $R^{15}$, $R^{16}$ and $R^{17}$ are independently hydrogen or a short chain alkyl having from 1 to 8 carbon atoms, or from 1 to 5 carbon atoms, or from 1 to 2 carbon atoms; n is an integer having a value of from 1 to 8, or 1 to 4; and X is a counterion. The nitrogen attached to $R^{15}$, $R^{16}$ and $R^{17}$ can be a protonated amine (primary, secondary or tertiary), but can also be a quaternary ammonium wherein each of $R^{15}$, $R^{16}$ and $R^{17}$ are alkyl groups. In certain embodiments, the cationic monomer can be polymethyacrylamidopropyl trimonium chloride, available under the trade name Polycare 133, from Rhone-Poulenc, Cranberry, N.J., U.S.A. In certain embodiment, copolymers of the cationic monomer are also suitable. In such embodiments, the charge density of the total copolymer can be from about 2.0 to about 4.5 meq/gm.

Other cationic polymers are also suitable including polysaccharide polymers, such as cationic cellulose derivatives and cationic starch derivatives. Suitable cationic polysaccharide polymers include those which conform to Formula IV:

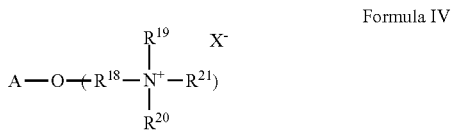

Formula IV wherein A is an anhydroglucose residual group, such as a starch or cellulose anhydroglucose residual; $R^{18}$ is an alkylene oxyalkylene, polyoxyalkylene, or hydroxyalkylene group, or combination thereof; $R^{19}$, $R^{20}$, and $R^{21}$ are independently alkyl, aryl, alkylaryl, arylalkyl, alkoxyalkyl, or alkoxyaryl groups, wherein each group contains up to 18 carbon atoms, and the total number of carbon atoms for each cationic moiety (i.e., the sum of carbon atoms in $R^{19}$, $R^{20}$, and $R^{21}$) is 20 or less; and X is an anionic counterion.

In certain embodiments, a cationic cellulose polymer can be selected from the salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable cationic cellulose polymers can include polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers can include cationic guar gum derivatives, such as guar hydroxypropyltrimonium chloride. Additional examples of suitable cationic guar gum derivatives can include the Jaguar series commercially available from Rhone-Poulenc Incorporated and the N-Hance series commercially available from Aqualon Division of Hercules, Inc. Additional details about cationic guar gum derivatives are disclosed in U.S. Pat. No. 6,930,078 which is incorporated by reference herein.

As can be appreciated, other cationic polymers known in the personal care industry are also suitable. For example, quaternary nitrogen-containing cellulose ethers are suitable. Examples of quaternary nitrogen-containing cellulose ethers are described in U.S. Pat. No. 3,962,418, which is incorporated herein by reference.

In certain embodiments, a synthetic cationic polymer or derivative thereof can be useful as a cationic polymer. Generally, such synthetic cationic polymers can be included at a concentration of from about 0.025% to about 5%, by weight of a personal care composition.

Suitable synthetic cationic polymers can include polymers which are water-soluble or dispersible, are cationic, and are non-crosslinked. In certain embodiments, suitable polymers can be conditioning copolymers comprising: (i) one or more cationic monomer units; and (ii) one or more nonionic monomer units or monomer units bearing a terminal negative charge; wherein said copolymer has a net positive charge. In certain embodiments, the synthetic cationic polymers can have a cationic charge density of from about 0.5 meq/g to about 10 meg/g, and can have an average molecular weight from about 1,000 to about 5,000,000.

Non-limiting examples of suitable synthetic cationic deposition polymers are described in United States Patent Application Publication No. US 2003/0223951 which is incorporated herein by reference.

Other suitable cationic polymers include copolymers of etherified cellulose, guar and starch, some examples of which are described in U.S. Pat. No. 3,958,581, which is incorporated herein by reference. Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference.

In embodiments including a cationic polymer, the cationic polymers can be soluble in the composition or can be soluble in a complex coacervate phase in the composition formed by interaction of the cationic polymer and a sulfate-free anionic, amphoteric or zwitterionic detersive surfactant. Complex coacervates of the cationic polymer can also be formed with other anionic charged materials in the personal care composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164 which is incorporated herein by reference.

Dispersed Particles

In certain embodiments, dispersed particles as known in the art can be included in a personal care composition. In embodiments including such dispersed particles, the particles can be incorporated, by weight of the composition, at levels of about 0.025% or more, about 0.05% or more, about 0.1% or more, about 0.25% or more, and about 0.5% or more. However, the personal care compositions can also contain, by weight of the composition, about 20% or fewer dispersed particles, about 10% or fewer dispersed particles, about 5% or fewer dispersed particles, about 3% or fewer dispersed particles, and about 2% or fewer dispersed particles.

Nonionic Polymers

The personal care compositions can also optionally include nonionic polymers. For example, polyalkylene glycols having a molecular weight of more than about 1000 can be useful to include in a personal care composition. Polyalkylene glycols can have the general formula V:

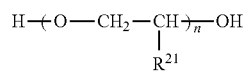

Formula V wherein $R^{21}$ is selected from the group consisting of H, methyl, and mixtures thereof. Specific polyethylene glycol polymers which are suitable include PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Conditioning Agents

Consumers sometimes prefer to purchase personal care compositions which provide both a cleaning benefit and a conditioning benefit. The inclusion of conditioning agents can allow for personal care compositions to be a "2 in 1" conditioning shampoo composition which both cleans and conditions hair. Generally, conditioning agents can include any material which provides a particular conditioning benefit to hair and/or skin. For example, in hair treatment compositions, suitable conditioning agents are those which deliver one or more benefits related to shine, softness, compatibility, antistatic properties, wet-handling, damage, manageability, body, and greasiness. In certain embodiments, suitable conditioning agents can include water insoluble, water dispersible, non-volatile, liquids that are emulsified into liquid particles or which are solubilized by the sulfate-free detersive surfactant. For example, a dimethicone or dimethiconol silicone agent can be included in certain embodiments.

In certain embodiments, suitable conditioning agents can generally include compounds classified as silicones or silicone derivatives (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the sulfate-free detersive surfactant. Generally any such conditioning agent can be suitable if it is physically and chemically compatible with the essential components of the personal care composition, and does not otherwise unduly impair product stability, aesthetics or performance.

The concentration of a conditioning agent in a personal care composition can be sufficient to provide the desired conditioning benefits. Such concentrations can vary with the conditioning agent, the conditioning performance desired, the average size of the conditioning agent particles, the type and concentration of other components, and other like factors. For example, inclusion of a cationic polymer to form a coacervate can improve the deposition of a conditioning agent. Optimization of conditioning agent concentration is generally known in the art.

1. Silicones

In embodiments where the conditioning agent is a silicone or silicone derivative, suitable silicone agents can include volatile silicone agents, non-volatile silicone agents, or a combination thereof. In certain embodiments, non-volatile silicone conditioning agents are preferred. If volatile silicones are present, the volatile agents will typically be incidental to their use as a solvent or carrier for non-volatile silicone materials ingredients, such as silicone gums and resins. In certain embodiments, the silicone conditioning agent particles can include a silicone fluid conditioning agent and other ingredients, such as a silicone resin to improve silicone fluid deposition efficiency or enhance glossiness of the hair.

The concentration of a silicone conditioning agent can range from about 0.01% to about 10%, by weight of the composition, from about 0.1% to about 8%, from about 0.1% to about 5%, and from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, each of which is hereby incorporated by reference herein. Suitable silicone conditioning agents can have a viscosity, as measured at about 25° C., from about 20 to about 2,000,000 centistokes ("csk"), from about 1,000 to about 1,800,000 csk, from about 50,000 to about 1,500,000 csk, and from about 100,000 to about 1,500,000 csk. The dispersed silicone conditioning agent particles can have a volume average particle diameter ranging from about 0.01 µm to about 50 µm. For small particle application to hair, the volume average particle diameters can range from about 0.01 µm to about 4 µm, from about 0.01 µm to about 2 µm, and from about 0.01 µm to about 0.5 µm. For larger particle application to hair, the volume average particle diameters can range from about 5 µm to about 125 µm, from about 10 µm to about 90 µm, from about 15 µm to about 70 µm, and from about 20 µm to about 50 µm.

Additional details about suitable silicone materials including silicone fluids, gums, and resins, as well as manufacture of silicones, are disclosed in *Encyclopedia of Polymer Science and Engineering*, vol. 15, 2d ed., pp 204-308, John Wiley & Sons, Inc. (1989), which is hereby incorporated by reference herein.

a. Silicone Oils

Suitable silicone fluids can include silicone oils which are flowable silicone materials having a viscosity, as measured at 25° C., or less than 1,000,000 csk, from about 5 csk to about 1,000,000 csk, and from about 100 csk to about 600,000 csk. Suitable silicone oils can include polyalkyl siloxanes, polyaryl siloxanes, polyalkylaryl siloxanes, polyether siloxane copolymers, and mixtures thereof. Other insoluble, non-volatile silicone fluids having hair conditioning properties can also be used.

For example, suitable silicone oils can include polyalkyl or polyaryl siloxanes which conform to Formula VI:

Formula VI

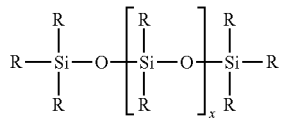

wherein each R is aliphatic, preferably alkyl or alkenyl, or aryl, R can be substituted or unsubstituted, and x is an integer from 1 to about 8,000. Suitable R groups can include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Suitable alkyl and alkenyl substituents are $C_1$ to $C_5$ alkyls and alkenyls, $C_1$ to $C_4$ alkyls and alkenyls, and $C_1$ to $C_2$ alkyls and alkenyls. The aliphatic portions of other alkyl-, alkenyl-, or alkynyl-containing groups (such as alkoxy, alkaryl, and alkamino) can be straight or branched chains, and can be $C_1$ to $C_5$, $C_1$ to $C_4$, $C_1$ to $C_3$, or from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described herein.

b. Amino and Cationic Silicones

Cationic silicone fluids suitable for use in the personal care compositions described herein can include silicone fluids described by general Formula VII:

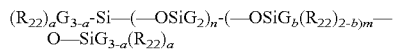

wherein G is hydrogen, phenyl, hydroxy, or $C_1$-$C_8$ alkyl, preferably methyl; a is 0 or an integer having a value from 1 to 3 or 0; b is 0 or 1; n is a number from 0 to 1,999 or 49 to 499; m is an integer from 1 to 2,000 or from 1 to 10; the sum of n and m is a number from 1 to 2,000, or from 50 to 500; $R_{22}$ is a monovalent radical conforming to the general formula $CqH_{2q}L$, wherein q is an integer having a value from 2 to 8 and L is selected from the following groups:

—N($R^{23}$)$CH_2$—$CH_2$—N($R^{23}$)$_2$

—N($R^{23}$)$_2$

—N($R^{23}$)$_3$A$^-$

—N($R^{23}$)$CH_2$—$CH_2$—NR$^{23}$H$_2$A$^-$ wherein $R^{23}$ is hydrogen, phenyl, benzyl, or a saturated hydrocarbon radical, preferably an alkyl radical from about $C_1$ to about $C_{20}$, and A$^-$ is a halide ion.

In certain embodiments, an amino silicone can be a cationic silicone known as "trimethyl-silylamodimethicone", which is shown below in Formula VIII:

Formula VIII

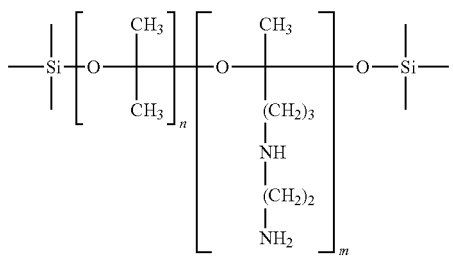

Other silicone cationic polymers which can be included include those described by Formula IX:

Formula IX

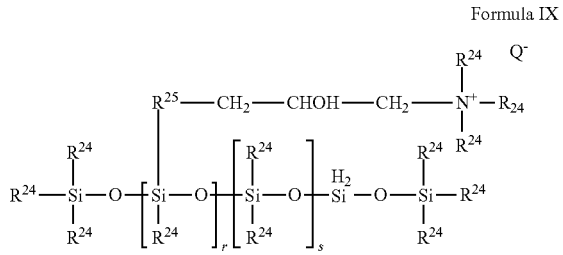

wherein $R^{24}$ is a monovalent hydrocarbon radical from $C_1$ to $C_{18}$ such as an alkyl or alkenyl radical, such as methyl; $R^{25}$ is a hydrocarbon radical, such as a $C_1$ to $C_{18}$ alkylene radical or a $C_{10}$ to $C_{18}$ alkyleneoxy radical or a $C_1$ to $C_8$ alkyleneoxy radical; Q$^-$ is a halide ion, such as chloride; r is an average statistical value from 2 to 20 or from 2 to 8; s is an average statistical value from 20 to 200 or from 20 to 50. An example of a suitable silicone cationic polymer of Formula IX is UCARE SILICONE ALE56™, available from Union Carbide.

c. Silicone Gums

Other silicone fluids suitable for use in a personal care composition include insoluble silicone gums. Such gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76, each of which are incorporated herein by reference. Specific examples of suitable silicone gums include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in a personal care composition include "high refractive index silicones," having a refractive index of about 1.46 or more, about 1.48 or more, about 1.52 or more, and about 1.55 or more. The refractive index of the polysiloxane fluid can also generally be less than about 1.70, or less than about 1.60. In this context, polysiloxane "fluid" includes oils as well as gums.

The high refractive index polysiloxane fluid includes those represented by general Formula VI above, as well as cyclic polysiloxanes such as those represented by Formula X below:

Formula X

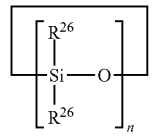

wherein $R^{26}$ is aliphatic, preferably alkyl or alkenyl, or aryl, $R^{26}$ can be substituted or unsubstituted, and n is a number from about 3 to about 7 or from about 3 to about 5.

A high refractive index polysiloxane fluid can contain an amount of aryl-containing $R^{26}$ substituents sufficient to increase the refractive index to the desired level. In certain embodiments, $R^{26}$ and n can be selected so that the material is non-volatile. Suitable aryl-containing substituents can include those which contain alicyclic and heterocyclic five and six member aryl rings and those which contain fused five or six member rings. The aryl rings themselves can be substituted or unsubstituted.

Generally, the high refractive index polysiloxane fluids can have a degree of aryl-containing substituents of about 15% or greater, about 20% or greater, about 25% or greater, about 35% or greater, or about 50% or greater. Typically, the degree of aryl substitution can be about 90% or less, and about 85% or less. In certain embodiments, the degree of aryl-containing substituents can vary from about 55% to about 80%.

In certain embodiments, high refractive index polysiloxane fluids can have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^{27}$NHR$^{28}$NH2 wherein each $R^{27}$ and $R^{28}$ independently is a $C_1$-$C_3$ alkyl, alkenyl, and/or alkoxy).

When high refractive index silicones are included in a personal care composition, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Suitable silicone fluids are also disclosed in U.S. Pat. Nos. 2,826,551, 3,964,500, 4,364,837, British Pat. No. 849,433, and *Silicon Compounds*, Petrarch Systems, Inc. (1984), all of which are incorporated herein by reference.

e. Silicone Resins

Silicone resins can be included in certain embodiments. As can be appreciated, such resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, a silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence.

In certain embodiments, suitable silicone resins can include MQ, MT, MTQ, MDT, and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

In certain embodiments, a conditioning component of a personal care composition can further include about 0.05% to about 3%, about 0.08% to about 1.5%, or 0.1% to about 1%, by weight of the composition, of at least one organic conditioning oil. The organic conditioning oil can be used either alone or in combination with other conditioning agents, such as a silicone.

a. Hydrocarbon Oils

Suitable organic conditioning oils can include hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be about $C_{12}$ to about $C_{19}$ in length in certain embodiments. Branched chain hydrocarbon oils, including hydrocarbon polymers, can contain more than 19 carbon atoms.

Specific examples of suitable hydrocarbon oils can include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which can include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers can include polybutene and polydecene. A hydrocarbon polymer can be polybutene, such as the copolymer of isobutylene and butene. A commercially available material of this type is L-14 polybutene from Amoco Chemical Corporation. The concentration of such hydrocarbon oils in the composition preferably range from about 0.05% to about 20%, more preferably from about 0.08% to about 1.5%, and even more preferably from about 0.1% to about 1%, by weight of the composition.

b. Polyolefins

Organic conditioning oils can also include liquid polyolefins such as liquid poly-α-olefins. In certain embodiments, a liquid polyolefin can be a hydrogenated liquid poly-α-olefins. Polyolefins for use herein are prepared by polymerization of $C_4$ to about $C_{14}$ or $C_6$ to about $C_{12}$ olefenic monomers.

Examples of suitable olefenic monomers can include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. In certain embodiments, it can be advantageous for the hydrogenated α-olefin monomers to be 1-hexene to 1-hexadecenes, 1-octene to 1-tetradecene, and mixtures thereof.

c. Fatty Esters

Other suitable organic conditioning oils can include fatty esters having at least 10 carbon atoms. Such fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof can include or have covalently bonded thereto other compatible functionalities, such as amides and alkoxy moieties (e.g., ethoxy or ether linkages, etc.).

Specific examples of suitable fatty esters can include: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in a personal care composition can include mono-carboxylic acid esters of the general formula R'COOR, wherein R' and R are alkyl or alkenyl radicals, and the sum of carbon atoms in R' and R is at least 10, preferably at least 22.

Still other fatty esters suitable for inclusion are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific examples of suitable di- and tri-alkyl and alkenyl esters of carboxylic acids can include isocetyl stearyol stearate, diisopropyl adipate, and tristearyl citrate.

Other fatty esters suitable are those known as polyhydric alcohol esters. Such polyhydric alcohol esters can include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, ethylene glycol distearate, polyoxyethylene polyol fatty acid ester, sorbitan fatty acid esters, and polyoxyethylene sorbitan fatty acid esters.

Still other fatty esters suitable for a personal care composition include glycerides. For example, mono-, di-, and tri-glycerides, preferably di- and tri-glycerides are suitable. In certain embodiments, the glycerides can be mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils can also be used including triolein and tristearin glyceryl dilaurate.

Other fatty esters suitable for use in the compositions of the present invention are water insoluble synthetic fatty esters described by Formula XI:

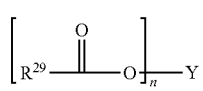

Formula XI wherein $R^{29}$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula XII:

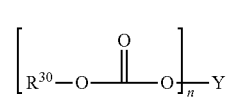

Formula XII wherein $R^{30}$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (XI).

In certain embodiments, synthetic fatty esters suitable for a personal care composition can include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

3. Other Conditioning Agents

As can be appreciated, a variety of additional conditioning agents are suitable as known in the art. For example, the conditioning agents described by the Procter & Gamble Company in U.S. Pat. Nos. 5,674,478, and 5,750,122 are suitable and both patents are incorporated herein by reference. Also suitable are the conditioning agents described in U.S. Pat. Nos. 4,529,586, 4,507,280, 4,663,158, 4,197,865, 4,217,914, 4,381,919, and 4,422,853, each of which is incorporated herein by reference.

Anti-Dandruff Actives

In certain embodiments, a personal care composition can also contain an anti-dandruff agent. Suitable anti-dandruff agents can include pyridinethione salts, azoles, selenium sulfide, particulate sulfur, and mixtures thereof. In certain embodiments, pyridinethione salts can be preferred. Such anti-dandruff particulate should be physically and chemically compatible with the essential components of the composition, and should not otherwise unduly impair product stability, aesthetics or performance. In certain embodiments, a personal care composition can include a cationic polymer to enhance deposition of an anti-dandruff active.

a. Pyridinethione Salts

In certain embodiments, an anti-dandruff agent can be a pyridinethione particulate such as a 1-hydroxy-2-pyridinethione salt. The concentration of pyridinethione anti-dandruff particulates can range from about 0.1% to about 4%, about 0.1% to about 3%, and from about 0.3% to about 2% by weight of the composition. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form, wherein the particles have an average size of up to about 20μ, preferably up to about 5μ, more preferably up to about 2.5μ. Salts formed from other cations, such as sodium, can also be suitable. Pyridinethione anti-dandruff agents are further described in U.S. Pat. Nos. 2,809,971; 3,236,733; 3,753,196; 3,761,418; 4,345,080; 4,323,683; 4,379,753; and 4,470,982, each of which are incorporated herein by reference. It is contemplated that when ZPT is used as the anti-dandruff particulate, that the growth or re-growth of hair may be stimulated or regulated, or both, or that hair loss may be reduced or inhibited, or that hair may appear thicker or fuller.

b. Other Anti-Microbial Actives

In addition to the anti-dandruff active selected from polyvalent metal salts of pyrithione, a personal care composition can further include one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. In certain embodiments, preferred anti-microbials can include itraconazole, ketoconazole, selenium sulphide and coal tar.

c. Azoles

In certain embodiments, a suitable anti-microbial agent can be an azole. Examples of azole anti-microbials can include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in a personal care composition, the azole anti-microbial active can be included in an amount from about 0.01% to about 5%, from about 0.1% to about 3%, and more from about 0.3% to about 2%, by weight of the composition. In certain embodiments, a ketoconazole azole can be preferred.

d. Selenium Sulfide

Selenium sulfide is a particulate anti-dandruff agent suitable for use as an anti-microbial compositions when included at concentrations of about 0.1% to about 4%, by weight of the composition, from about 0.3% to about 2.5% by weight, and from about 0.5% to about 1.5% by weight. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. Nos. 2,694,668; 3,152,046; 4,089,945; and 4,885,107, each of which are incorporated herein by reference.

e. Sulfur

Sulfur can also be used as a particulate anti-microbial/anti-dandruff agent in certain embodiments. Effective concentrations of the particulate sulfur are typically from about 1% to about 4%, by weight of the composition, preferably from about 2% to about 4%.

f. Keratolytic Agents

Keratolytic agents such as salicylic acid can also be included in a personal care composition described herein.

g. Other

Additional anti-microbial actives can include extracts of melaleuca (tea tree) and charcoal. As can be appreciated, personal care compositions can also include combinations of anti-microbial actives. Suitable combinations can include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Humectant

A personal care composition can also include a humectant to lower the rate of water evaporation. Suitable humectants can include polyhydric alcohols, water soluble alkoxylated nonionic polymers, and mixtures thereof. The humectants, when included, can be used at levels by weight of the composition of from about 0.1% to about 20%, and from about 0.5% to about 5%.

Suitable polyhydric alcohols can include glycerin, sorbitol, propylene glycol, butylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Suitable water soluble alkoxylated nonionic polymers can include polyethylene glycols and polypropylene glycols having a molecular weight of up to about 1000 such as those with CTFA names PEG-200, PEG-400, PEG-600, PEG-1000, and mixtures thereof.

Suspending Agent

In certain embodiments, a personal care composition can include a suspending agent at concentrations effective for suspending water-insoluble material in dispersed form in the compositions or for modifying the viscosity of the composition. Such concentrations range from about 0.1% to about 10%, and from about 0.3% to about 5.0%, by weight of the compositions.

Suitable suspending agents can include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Other suitable suspending agents can include crystalline suspending agents which can be categorized as acyl derivatives, long chain amine oxides, and mixtures thereof. Examples of such suspending agents are described in U.S. Pat. No. 4,741,855, which is incorporated herein by reference. Suitable suspending agents include ethylene glycol esters of fatty acids having from 16 to 22 carbon atoms. In certain embodiments, the suspending agent can be an ethylene glycol stearates, both mono and distearate, but particularly the distearate containing less than about 7% of the mono stearate. Other suitable suspending agents include alkanol amides of fatty acids, preferably having from 16 to 22 carbon atoms, more preferably 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Viscosity Modifiers

Viscosity modifiers can be used to modify the rheology of a personal care composition. Suitable viscosity modifiers can include carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol. Sodium chloride and sodium xylene sulfonate can also be used as a viscosity modifier. Other suitable rheology modifiers can include cross-linked acrylates, cross-linked maleic anhydride co-methylvinylethers, hydrophobically modified associative polymers, and mixtures thereof.

Other Optional Components

As can be appreciated, a personal care composition can include still further optional components. For example, amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

In certain embodiments, a personal care composition can optionally include pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions can also include antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

In certain embodiments, one or more stabilizers and preservatives can be included. For example, one or more of trihydroxystearin, ethylene glycol distearate, citric acid, sodium citrate dihydrate, a preservative such as kathon, sodium chloride, sodium benzoate, and ethylenediaminetetraacetic acid ("EDTA") can be included to improve the lifespan of a personal care compositon.

Chelants can also be included to scavenge metal and reduce hair damage caused by exposure to UV radiation. Examples of suitable chelants can include histidine and N,N' ethylenediamine disuccinic acid ("EDDS").

Multi-Phase Compositions

In certain embodiments, a personal care composition can include two or more phases to make a multiphase personal care composition. In such embodiments, one phase can include traditional personal care components, such as structured surfactants, and a second phase of the multiphase personal care compositions can include a benefit phase. Details of components and methods of making a multi-phase personal care composition are disclosed in U.S. Pat. No. 8,653,014 which is incorporated herein by reference.

Method of Making a Personal Care Composition

A personal care composition described herein can be formed similarly to known personal care compositions. For example, the process of making a personal care composition can include (a) combining a fatty alcohol, a gel network surfactant, and water at a temperature sufficient to allow partitioning of the secondary surfactant and the water into the fatty alcohol to form a pre-mix; (b) cooling the pre-mix below the chain melt temperature of the fatty alcohol to form a gel network; (c) adding the gel network to one or more detersive surfactants and a liquid carrier to form a personal care composition which includes a dispersed gel network phase having a melt transition temperature of at least about 38° C.

In certain embodiments, a dispersed gel network phase can be formed as a separate pre-mix, which, after being cooled, can be subsequently incorporated with the other components of a personal care composition. More specifically, the gel network phase can be prepared by heating the fatty alcohol, the gel network surfactant, and water to a level in the range of about 75° C. to about 90° C. and mixing. This mixture can be cooled to a level in the range of about 27° C. to about 35° C. by, for example, passing the mixture through a heat exchanger. As a result of this cooling step, at least about fifty percent of the mixture of the fatty alcohol and the gel network surfactant crystallize to form a crystalline gel network.

Alternative methods of preparing the gel network phase include sonication and/or milling of the fatty alcohol, the gel network surfactant, and water, while these components are heated, to reduce the particle size of the dispersed gel network phase. This results in an increase in surface area of the gel network phase, which allows the gel network surfactant and the water to swell the gel network phase. Another suitable variation in preparing the gel network includes heating and mixing the fatty alcohol and the gel network surfactant first, and then adding that mixture to the water.

Method of Use

The personal care compositions described herein can be used in a conventional manner for cleansing and conditioning of hair or skin. Generally, a method of treating hair or skin can include applying the personal care composition to the hair or skin. For example, an effective amount of the personal care composition can be applied to the hair or skin, which has been wetted with water, and then the composition can be rinsed off. Effective amounts can generally range from about 1 g to about 50 g in certain embodiments, and from about 1 g to about 20 g in certain embodiments. Application to the hair typically includes working the composition through the hair such that most or all of the hair is contacted with the composition.

In certain embodiments, a method for treating the hair or skin can include the steps of: (a) wetting the hair or skin with water; (b) applying an effective amount of the personal care composition to the hair or skin, and (c) rinsing the applied areas of skin or hair with water. These steps can be repeated as many times as desired to achieve the desired cleansing and conditioning benefit.

In certain embodiments, a personal care composition as described herein can be used to treat damaged hair. Damaged hair can include hair permed hair, oxidatively colored hair, and mechanically damaged hair.

The personal care compositions can be used as liquids, solids, semi-solids, flakes, gels, in a pressurized container with a propellant added, or used in a pump spray form. The viscosity of the product may be selected to accommodate the form desired.

NON-LIMITING EXAMPLES

The personal care compositions illustrated in the following Examples illustrate specific embodiments of the personal care compositions described herein, but are not intended to be limiting thereof. Other modifications can be undertaken by the skilled artisan without departing from the spirit and scope of this invention. These exemplified embodiments of the personal care composition provide suitable cleaning benefits to hair without the use of a harsh sulfate-based surfactant The personal care compositions illustrated in the following Examples are prepared by conventional formulation and mixing methods, an example of which is set forth below. All exemplified amounts are listed as weight percent's and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix of Table 1, water is heated to about 74° C. and the fatty alcohol and gel network surfactant are added to it in the quantities depicted in Table 1. After incorporation, this mixture is passed through a mill and heat exchanger where it is cooled to about 32° C. As a result of this cooling step, the fatty alcohol, the gel network surfactant, and the water form a crystalline gel network.

TABLE 1

| Premix | % |
|---|---|
| Gel Network Surfactant[1] | 11.00 |
| Stearyl Alcohol | 8% |
| Cetyl Alcohol | 4% |
| Water | QS |

[1]For anionic gel networks, suitable gel networksurfactants above include surfactants with a net negative charge including sulfonates, carboxylates and phosphates among others and mixtures thereof.

For cationic gel networks, suitable gel network surfactants above include surfactants with a net positive charge including quaternary ammonium surfactants and mixtures thereof.

For Amphoteric or Zwitterionic gel networks, suitable gel network surfactants above include surfactants with both a positive and negative charge at product usage pH including betaines, amine oxides, sultaines, amino acids among others and mixtures thereof.

Preparation of Final Personal Care Compositions

Final personal care compositions can be prepared by adding the gel network premix previously formed from the components of Table 1 to the components of Tables 2 through 4. Several Example formulations were produced as depicted in Tables 2 through 4. Inventive Examples 1 to 12 each included a gel network while Comparative Examples 1 and 2 did not.

Tables 2 through 4 depict the active weight percentages of each component included in the Example formulations. The gel network premix levels depicted in Tables 2 through 4 indicate the combined weight percent of the active gel network surfactant and the active fatty material in the final composition as added from the gel network premixes of Table 1.

TABLE 2

| Components | Comp. Ex. 1 | Comp. Ex. 2 | Inv. Ex. 1 | Inv. Ex. 2 | Inv. Ex. 3 |
|---|---|---|---|---|---|
| Water-USP Purified & Minors | Q.S. to 100 | Q.S. to 100 | Q.S. to 100 | Q.S. to 100 | Q.S. to 100 |
| Surfactants | | | | | |
| Sodium Laureth Sulfate (SLE1S) | — | 14 | — | — | — |
| Sodium Lauryl Sulfate (SLS) | — | 1.5 | — | — | — |
| Cocoamidopropyl Betaine (CapB) | — | 1.7 | — | — | — |
| Sodium Cocoamphoacetate | 6 | — | 6 | 6 | 6 |
| Lauryl Sulfosuccinate | 5 | — | 5 | 5 | 5 |
| Decyl Glucoside | 5 | — | 5 | 5 | 5 |
| Gel Network (Table 1) | | | | | |
| Cationic Gel Network | — | — | 5 | — | — |
| Anionic Gel Network | — | — | — | 5 | — |

TABLE 2-continued

| Components | Comp. Ex. 1 | Comp. Ex. 2 | Inv. Ex. 1 | Inv. Ex. 2 | Inv. Ex. 3 |
|---|---|---|---|---|---|
| Amphoteric Gel Network | — | — | — | — | 5 |
| Other | | | | | |
| Guar Hydroxypropyltrimonium Chloride | — | 0.3 | — | — | — |
| Polyquaternium 6 (DADMAC) | 0.5 | 0.1 | 0.5 | 0.5 | 0.5 |
| Ethylene Glycol Distearate | — | 1.5 | — | — | — |
| Dimethicone/Dimethiconol | — | 1 | — | — | — |
| Citric Acid | 1 | 1 | 1 | 1 | 1 |
| Sodium Citrate Dihydrate | 1 | 1 | 1 | 1 | 1 |
| Acrylates/C10-C30 alkyl acrylate crosspolymers | 0.5 | — | 0.5 | 0.5 | 0.5 |
| Histidine | 0.1 | 0.1 | 0.1 | 0.1 | 0.1 |
| Kathon | 0.0005 | 0.0005 | 0.0005 | 0.0005 | 0.0005 |
| Sodium Benzoate | 0.25 | 0.25 | 0.25 | 0.25 | 0.25 |
| Disodium EDTA | 0.1 | 0.1 | 0.1 | 0.1 | 0.1 |
| Perfume | 0.8 | 0.8 | 0.8 | 0.8 | 0.8 |
| Sodium Chloride* | 0-3 | 0-3 | 0-3 | 0-3 | 0-3 |
| Sodium Xylene Sulfonate* | 0-3 | 0-3 | 0-3 | 0-3 | 0-3 |

*Indicates that the levels were adjusted to reach the desired viscosity.

TABLE 3

| Components | Inv. Ex. 4 | Inv. Ex. 5 | Inv. Ex. 6 | Inv. Ex. 7 | Inv. Ex. 8 | Inv. Ex. 9 |
|---|---|---|---|---|---|---|
| Water-USP Purified & Minors | Q.S. to 100 | Q.S. to 100 | Q.S. to 100 | Q.S. to 100 | Q.S. to 100 | Q.S. to 100 |
| Surfactants | | | | | | |
| Cocoamidopropyl Betaine (CapB) | 1 | 1 | 1 | 5 | 5 | 5 |
| Sodium Cocoyl Isethionate | 6 | 6 | 6 | — | — | — |
| Disodium Laureth Sulfosuccinate | 6 | 6 | 6 | — | — | — |
| Decyl Glucoside | 1 | 1 | 1 | — | — | — |
| Cocoamide Monoethanolamine | — | — | — | 3 | 3 | 3 |
| Sodium Lauroyl Sarcosinate | 3 | 3 | 3 | 5 | 5 | 5 |
| Gel Network (Table 1) | | | | | | |
| Cationic Gel Network | 5 | — | — | 5 | — | — |
| Anionic Gel Network | — | 5 | — | — | 5 | — |
| Amphoteric Gel Network | — | — | 5 | — | — | 5 |
| Other | | | | | | |
| Guar Hydroxypropyltrimonium Chloride | 0.5 | 0.3 | 0.5 | 0.5 | 0.3 | 0.5 |
| Polyquaternium 6 (DADMAC) | — | 0.1 | — | — | 0.1 | — |
| Ethylene Glycol Distearate | — | 1.5 | — | — | 1.5 | — |
| Dimethicone/Dimethiconol | 1 | 1 | — | 1 | 1 | — |
| Citric Acid | 1 | 1 | 1 | 1 | 1 | 1 |
| Sodium Citrate Dihydrate | 1 | 1 | 1 | 1 | 1 | 1 |
| Acrylates/C10-C30 alkyl acrylate crosspolymers | 0.5 | 0.5 | 0.5 | 0.5 | 0.5 | 0.5 |
| Histidine | 0.1 | 0.1 | 0.1 | 0.1 | 0.1 | 0.1 |
| Kathon | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 |
| Disodium EDTA | 0.1 | 0.1 | 0.1 | 0.1 | 0.1 | 0.1 |
| Perfume | 0.8 | 0.8 | 0.8 | 0.8 | 0.8 | 0.8 |
| Sodium Chloride* | 0-3 | 0-3 | 0-3 | 0-3 | 0-3 | 0-3 |
| Sodium Xylene Sulfonate* | 0-3 | 0-3 | 0-3 | 0-3 | 0-3 | 0-3 |

*Indicates that the levels were adjusted to reach the desired viscosity.

TABLE 4

| Components | Inv. Ex. 10 | Inv. Ex. 11 | Inv. Ex. 12 |
|---|---|---|---|
| Water-USP Purified & Minors | Q.S. to 100 | Q.S. to 100 | Q.S. to 100 |
| Surfactants | | | |
| Cocoamidopropyl Betaine (CapB) | 7 | 7 | 7 |
| Sodium Cocoyl Isethionate | 3 | 3 | 3 |
| Sodium Cocoamphoacetate | 4 | 4 | 4 |
| Decyl Glucoside | 1 | 1 | 1 |
| Sodium Cocoyl Glutamate | 1 | 1 | 1 |
| Gel Network (Table 1) | | | |
| Cationic Gel Network | 5 | — | — |
| Anionic Gel Network | — | 5 | — |
| Amphoteric Gel Network | — | — | 5 |
| Other | | | |
| Guar Hydroxypropyltrimonium Chloride | 0.5 | 0.3 | 0.5 |
| Polyquaternium 6 (DADMAC) | — | 0.1 | — |
| Ethylene Glycol Distearate | — | 1.5 | — |
| Dimethicone/Dimethiconol | 1 | 1 | — |
| Citric Acid | 1 | 1 | 1 |
| Sodium Citrate Dihydrate | 1 | 1 | 1 |
| Acrylates/C10-C30 alkyl acrylate crosspolymers | 0.5 | 0.5 | 0.5 |
| Histidine | 0.1 | 0.1 | 0.1 |
| Kathon | 0.0005 | 0.0005 | 0.0005 |
| Sodium Benzoate | 0.25 | 0.25 | 0.25 |
| Disodium EDTA | 0.1 | 0.1 | 0.1 |
| Perfume | 0.8 | 0.8 | 0.8 |
| Sodium Chloride* | 0-3 | 0-3 | 0-3 |
| Sodium Xylene Sulfonate* | 0-3 | 0-3 | 0-3 |

*Indicates that the levels were adjusted to reach the desired viscosity.

FIG. 1 depicts a picture of four hair samples which were soiled with human sebum to mimic soiled hair. A fluorescent dye was added to the sebum to track the degree of sebum removal after washing with several of the Example compositions of Table 2. The intensity of the fluorescent dye remaining after washing indicates the cleaning quality of the Example compositions to remove sebum with greater quantities of fluorescent dye remaining in the hair samples indicating poorer cleaning qualities. Each hair sample was a 40 g ponytail made from non-color treated hair obtained from the general population. Samples were washed with 10 g of each Example composition under controlled conditions including water flow, water hardness, and temperature control to mimic a consumer's typical hair washing habits. After rinsing, the samples were allowed to dry and then analyzed under fluorescent light.

FIG. 1 includes an unwashed control hair sample, a hair sample washed with Comparative Example 1, a hair sample washed with Comparative Example 2, and a hair sample washed with Inventive Example 1. As can be appreciated, Comparative Example 1 is a sulfate free personal care composition, Comparative Example 2 is a personal care composition including sulfated surfactants, and Inventive Example 1 is the sulfate free personal care composition of Comparative Example 1 but further including 5%, by active weight percent, of a sulfate free cationic dispersed gel network phase.

As illustrated by FIG. 1, the sulfate-free personal care composition of Comparative Example 1 provided poor cleaning and removed only 60% of the sebum. The addition of 5%, by active weight percent, of a sulfate free dispersed gel network phase to the composition as illustrated by Inventive Example 1 increased the cleaning effectiveness of the composition and removed 90% of the sebum. Inventive Example 1 also demonstrated better cleaning effectiveness and sebum removal than the traditional cosmetic shampoo of Comparative Example 2 which removed only 80% of the sebum.

It will be appreciated that other modifications of the present disclosure are within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified. A level of perfume and/or preservatives may also be included in the following examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

Examples of personal care compositions and methods as described herein include the compositions described by paragraphs A to T and combinations thereof:

A. A personal care composition comprising:
    a dispersed gel network comprising:
        about 0.05% or more, by weight of the personal care composition, of one or more fatty alcohols,
        about 0.01% or more, by weight of the personal care composition, of a gel network surfactant, the gel network surfactant selected from a first group consisting of anionic surfactants, cationic surfactants, amphoteric surfactants, zwitterionic surfactants, non-ionic surfactants, and mixtures thereof; and
        water;
    a detersive surfactant selected from a second group consisting of an anionic surfactants, cationic surfactants, amphoteric surfactants, zwitterionic surfactants, non-ionic surfactants, and mixtures thereof; and
    liquid carrier; and
    wherein the personal care composition is substantially free of sulfated surfactants.

B. The personal care composition according to paragraph A, wherein the gel network surfactant and the detersive surfactant each independently comprise an isethionate, a sarcosinate, a sulfonate, a sulfosuccinate, a sulfoacetate, a glycinate, a glutamate, an ester, a carboxylate, an amphoacetate, a taurate, an acyl amino acid, a betaine, a sultaine, or a mixture thereof.

C. A personal care composition according to paragraph A or B, wherein the gel network surfactant comprises a phosphate ester.

D. A personal care composition according to any preceding paragraph A-C, wherein the gel network surfactant comprises one or more of cetrimonium chloride, stearimonium chloride, behentrimonium chloride, behentrimonium methosulfate, behenamidopropyltrimonium methosulfate, stearamidopropyltrimonium chloride, arachidtrimonium chloride, and distearyldimonium chloride.

E. A personal care composition according to any preceding paragraph A-D, wherein the gel network surfactant and the detersive surfactant are different.

F. A personal care composition according to any preceding paragraph A-E comprising about 5% or more, by weight of the personal care composition, of the detersive surfactant.

G. A personal care composition according to any preceding paragraph A-F, wherein the dispersed gel network further comprises one or more fatty compounds selected from the group consisting of fatty amides, di-fatty ethers, fatty carbamates, fatty acids, fatty esters, fatty phosphorus compounds, fatty sorbitan derivatives, alkyl sulfoxides, and mixtures thereof.

H. A personal care composition according to any preceding paragraph A-G, further comprising a stabilizing agent comprising one or more of trihydroxystearin, ethylene glycol distearate, citric, citrate, a preservative, sodium chloride, sodium benzoate, ethylenediaminetetraacetic acid ("EDTA") or a salt thereof.

I. A personal care composition according to any preceding paragraph A-H, wherein the one or more fatty alcohols comprise one or more of cetyl alcohol, stearyl alcohol, and behenyl alcohol.

J. The personal care composition according to any previous paragraph A-I, comprising about 5% to about 30%, by weight, of the detersive surfactant and gel network surfactant.

K. A personal care composition according to any previous paragraph A-J, further comprising a cationic polymer comprising one or more guar derivatives, synthetic derivatives, and cellulose derivatives.

L. A personal care composition according to any previous paragraph A-K, further comprising a silicone conditioning agent comprising one or more of dimethicone, dimethiconol, and an amino silicone.

M. A personal care composition according to any previous paragraph A-L, comprising about 1% to about 10%, by weight, of the one or more fatty alcohols and the gel network surfactant.

N. A personal care composition according to any previous paragraph A-M is a shampoo.

O. The personal care composition of paragraph N removes more oil from hair than a similar personal care composition formed without the dispersed gel network.

P. The personal care composition of paragraph N produces a higher volume of lather than a similar personal care composition formed without the dispersed gel network.

Q. The personal care composition according to any previous paragraph A-P is substantially free of sulfates.

R. A method of producing a personal care composition, the method comprising:
  a) combining one or more fatty alcohols and a gel network surfactant in a water solution in a weight ratio of about 1:10 to a ratio of about 40:1 at a temperature sufficient to allow partitioning of the gel network surfactant into the one or more fatty alcohols to form a mixture;
  b) cooling the mixture to a temperature below the chain melt temperature of the one or more fatty alcohols to form a gel network; and
  c) adding the gel network to a detersive surfactant and a liquid carrier to form a personal care composition; and
  wherein the personal care composition is substantially free of sulfated surfactants.

S. The method of paragraph R, wherein the gel network surfactant and the detersive surfactant each independently comprise an isethionate, a sarcosinate, a sulfonate, a sulfosuccinate, a sulfoacetate, a glycinate, a glutamate, an ester, a carboxylate, an amphoacetate, a taurate, quaternium, behenyltrimethylammonium chloride, or a mixture thereof.

T. A method of cleansing without sulfates, the method comprising:
  providing a personal care composition substantially free of sulfated surfactants comprising:
    a dispersed gel network comprising:
      about 0.05% or more, by weight of the personal care composition, of one or more fatty alcohols;
      about 0.01% or more, by weight of the personal care composition, of a gel network surfactant, the gel network surfactant selected from a first group consisting of anionic surfactants, cationic surfactants, amphoteric surfactants, zwitterionic surfactants, non-ionic surfactants, and mixtures thereof; and
      water; and
    a detersive surfactant selected from a second group consisting of an anionic surfactants, cationic surfactants, amphoteric surfactants, zwitterionic surfactants, non-ionic surfactants, and mixtures thereof; and
    liquid carrier; and
  forming a lather with water and the personal care composition to clean a substrate; and
  rinsing the lather out of the substrate.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
  about 5% of a dispersed gel network comprising: about 0.05% to about 1%, by weight of the personal care composition, of one or more fatty alcohols, wherein the one or more fatty alcohols comprise a combination of stearyl alcohol and cetyl alcohol,
  about 0.01% to about 1%, by weight of the personal care composition, of a gel network surfactant, wherein the gel network surfactant is selected from an isethionate, a sarcosinate and mixtures thereof, and
  water, wherein the gel network is dispersed in the personal care composition;
  about 5% to about 15%, by weight of the personal care composition, of an anionic surfactant selected from sodium lauroyl sarcosinate, a combination of sodium cocoamphoacetate and lauryl sulfosuccinate, a combination of sodium cocoyl isethionate, disodium laureth sulfosuccinate and sodium lauroyl sarcosinate, and a combination of sodium cocoyl isethioniate, sodium cocoamphoacetate and sodium cocoyl glutamate;
  about 0.1% to about 0.5%, by weight of the personal care composition, of a cationic polymer selected from polyquaternium-6, guar hydroxypropyltrimonium chloride, and a mixture thereof; and
  a liquid carrier.

2. The personal care composition of claim 1, wherein the personal care composition further comprises a chelant selected from histidine and N,N' ethylenediamine disuccinic acid.

3. The personal care composition of claim 2, wherein the chelant comprises histidine.

4. The personal care composition of claim 1, further comprising a stabilizing agent comprising one or more of trihydroxystearin, ethylene glycol distearate, citric, citrate, a preservative, sodium chloride, sodium benzoate, ethylenediaminetetraacetic acid ("EDTA") or a salt thereof.

5. The personal care composition of claim 1, further comprising a silicone conditioning agent comprising one or more of dimethicone, dimethiconol, and an amino silicone.

6. The personal care composition of claim 1, wherein the personal care composition is a shampoo.

7. The personal care composition of claim 6, wherein the shampoo produces a higher volume of lather than a similar personal care composition formed without the dispersed gel network.

8. The personal care composition of claim 1, wherein the gel network surfactant comprises an isethionate.

9. The personal care composition of claim 1, wherein the gel network surfactant is present at 0.01% to 5%, by weight of the personal care composition.

* * * * *